United States Patent
Galloway

(10) Patent No.: US 11,268,035 B2
(45) Date of Patent: Mar. 8, 2022

(54) PRODUCTION OF RENEWABLE FUELS AND ENERGY BY STEAM/CO2 REFORMING OF WASTES

(71) Applicant: Raven SR LLC, Pinedale, WY (US)

(72) Inventor: Terry R. Galloway, Berkeley, CA (US)

(73) Assignee: Raven SR, Inc., Pinedale, WY (US)

( * ) Notice: Subject to any disclaimer, the term of this patent is extended or adjusted under 35 U.S.C. 154(b) by 0 days.

(21) Appl. No.: 17/128,140

(22) Filed: Dec. 20, 2020

(65) Prior Publication Data

US 2021/0207036 A1 Jul. 8, 2021

Related U.S. Application Data

(63) Continuation of application No. 16/730,755, filed on Dec. 30, 2019, now Pat. No. 10,889,761, which is a
(Continued)

(51) Int. Cl.
*C10G 2/00* (2006.01)
*C10J 3/80* (2006.01)
(Continued)

(52) U.S. Cl.
CPC ............... *C10G 2/31* (2013.01); *C10J 3/005* (2013.01); *C10J 3/80* (2013.01); *C10J 3/84* (2013.01); *C10K 1/004* (2013.01); *C10K 1/005* (2013.01); *C10K 1/007* (2013.01); *C10K 1/022* (2013.01); *C10K 1/024* (2013.01); *C10K 3/006* (2013.01); *C01B 2203/0222* (2013.01); *C01B 2203/0283* (2013.01); *C01B 2203/061* (2013.01); *C01B 2203/062* (2013.01); *C01B 2203/1619* (2013.01); *C07C 29/1518* (2013.01); *C10J 2200/09* (2013.01); *C10J 2300/0916* (2013.01); *C10J 2300/0989* (2013.01); *C10J 2300/1659* (2013.01); *C10J 2300/1671* (2013.01); *C10J 2300/1675* (2013.01); *C10J 2300/1807* (2013.01); *C10J 2300/1815* (2013.01);
(Continued)

(58) Field of Classification Search
CPC ........ C10K 3/006; C10K 1/024; C10K 1/022; C10K 1/007; C10K 1/004; C10J 3/84; C10J 3/80; C10J 3/005; C10G 2/32
See application file for complete search history.

(56) References Cited

U.S. PATENT DOCUMENTS

2005/0256212 A1 11/2005 Norbeck et al.
2016/0152905 A1 6/2016 Kelfkens et al.

OTHER PUBLICATIONS

U.S. Appl. No. 16/240,349, Nonfinal Office Action, 8 pgs dated May 15, 2019.
(Continued)

*Primary Examiner* — Jafar F Parsa
(74) *Attorney, Agent, or Firm* — Dentons Bingham Greenebaum LLP; Brian W. Chellgren; John V. Daniluck

(57) ABSTRACT

This invention relates to a power recovery process in waste steam/$CO_2$ reformers in which a waste stream can be made to release energy without having to burn the waste or the syngas. This invention in some embodiments does not make use of fuel cells as a component but makes use of exothermic chemical reactors using syngas to produce heat, such as Fischer-Tropsch synthesis. It also relates to control or elimination of the emissions of greenhouse gases in the power recovery process of this invention with the goal of producing energy in the future carbonless world economy.

15 Claims, 17 Drawing Sheets

Related U.S. Application Data continuation of application No. 16/240,349, filed on Jan. 4, 2019, now Pat. No. 10,538,709.

(60) Provisional application No. 62/613,881, filed on Jan. 5, 2018.

(51) Int. Cl.
*C10K 1/00* (2006.01)
*C10K 1/02* (2006.01)
*C10J 3/84* (2006.01)
*C10J 3/00* (2006.01)
*C10K 3/00* (2006.01)
*C07C 29/151* (2006.01)

(52) U.S. Cl.
CPC ............. *C10J 2300/1884* (2013.01); *C10J 2300/1892* (2013.01)

(56) References Cited

OTHER PUBLICATIONS

U.S. Appl. No. 16/240,349, Applicant Response to Office Action, 10 pgs dated Aug. 14, 2019.
U.S. Appl. No. 16/240,349, Notice of Allowance, 8 pgs dated Sep. 9, 2019.
U.S. Appl. No. 16/730,755, Notice of Allowance 7 pgs dated Nov. 12, 2020.
U.S. Appl. No. 16/730,755, Nonfinal Office Action, 6 pgs dated Jun. 26, 2020.
U.S. Appl. No. 16/730,755, Applicant Response to Nonfinal Office Action, 6 pgs dated Oct. 26, 2020.

PRODUCTION OF RENEWABLE FUELS AND ENERGY BY STEAM/CO2 REFORMING OF WASTES

CROSS REFERENCE TO RELATED APPLICATION

This application is a continuation of U.S. application Ser. No. 16/730,755, filed Dec. 30, 2019, a continuation of U.S. application Ser. No. 16/240,349, filed Jan. 4, 2019, which claims the benefit of priority to U.S. Provisional Patent Application Ser. No. 62/613,881, filed Jan. 5, 2018, each of which are incorporated herein by reference.

FIELD OF THE INVENTION

The invention relates to a process and system in which a waste stream can be made to release energy without having to burn the waste or the syngas and consume oxygen and have large carbon dioxide emissions. In some embodiments the waste can be converted into a carbon-containing, carbon sequestering fertilizer, renewable hydrogen fuel, and products of important commercial value, such as unsaturated, high-density renewable fuels and paraffin wax.

BACKGROUND OF THE INVENTION

There is a great need to destroy a wide range of waste streams generated around the world and at the same time to convert this carbonaceous waste into useful hydrogen-rich syngas to accomplish one or more of the following: (1) production of renewable $H_2$ fuel, (2) to feed an exothermic hydrocarbon synthesis reactor, such as a Fischer-Tropsch unit (FT), to produce renewable fuels, or (3) to use a portion of this syngas to drive a fuel cell to power the plant.

This steam/$CO_2$-reforming chemistry used in the steam/$CO_2$ reformer (SR) does not involve combustion. The idealized main chemical reactions, which can be considered to be chemical reduction, occur from the RR through the SSR main reactor is as follows:

$$C_aH_bO_c + dCO_2 + (a-c-d)H_2O + HEAT \rightarrow (a+d)CO + (a+0.5b-c-d)H_2$$

and many more reactions into the hundreds:

$$C + 2H_2 \rightarrow CH_4$$

$$CH_4 + CO_2 + HEAT \rightarrow 2CO + 2H_2$$

$$C + H_2O \rightarrow CO + H_2$$

$$C + CO_2 \rightarrow 2CO + HEAT$$

$$H_2 + CO_2 \longleftrightarrow H_2O + CO$$

... etc.

Although the steam-reforming chemistry is just started in the rotary reformer, it continues to near completion as the gas temperature increases along its path through the system into the main steam/CO2 reforming reactor where more reaction occurs with superheated steam preferably without catalysts. This reaction with superheated steam has a residence time of less than about two seconds mainly at the elevated, nearly isothermal conditions in main reactor; in some embodiments there is not the very brief exposure to high temperatures typical of an incinerator flame region.

The challenge and problem with fuel cells has been their extreme sensitivity to various unknown chemical poisons at parts per million levels coming from the waste streams from harming the electrochemical catalysts of the high temperature fuel cells. By comparison Flory-Huggins catalysts in Fischer-Tropsch reactors (such as supported iron and cobalt catalysts) are much less sensitive to poisons than fuel cells and are highly exothermic.

$$CO + 2H_2 \rightarrow 1/n(-CH_2-)_n(I) + H_2O(I) \quad \Delta H°_{298} = -231.1 \text{ kJ/mol}$$

Conversion of syngas to methanol using copper catalysts in the gas phase or liquid-phase catalysts are exothermic and also less sensitive to poisons.

$$CO + 2H_2 \rightarrow CH_3OH(I) \quad \Delta H°_{298} = -128.2 \text{ kJ/mol}$$

There is syngas methanation that is highly exothermic:

$$2CO + 2H_2 \rightarrow CH_4 + CO_2 \quad \Delta H°_{298} = -247.3 \text{ kJ/mol}$$

So these three reactions listed above cause the FT chemistry to produce many other gases besides the hydrocarbons $[1/n(-CH_2-)_n(I)]$ desired. In some embodiments there is a minimization of these side reactions, or use of them, by reusing the FT tail gas through recycling back to the rotary reformer. The CO2 in Steam/CO2 reforming helps minimize this side reaction above.

All of these highly exothermic reactors produce high-grade useful energy, they all can convert syngas with enough exothermicity to make large amounts of electricity, steam and heat. These exothermic reactors can substitute for fuel cells. Thus, an aspect of some embodiments of the present invention include methods and process systems to convert waste to energy without burning the waste but to sequester the carbon of the waste so carbon gases are not released.

The composition of the syngas was determined in detail according to one embodiment of the present invention from a pilot plant where med-waste was steam/$CO_2$ reformed to make syngas. The syngas composition is shown in Table 1 below.

TABLE 1

Results from Pilot Plant Gas Test By Steam/$CO_2$ Reforming Of Solid Waste

| | | |
|---|---|---|
| $H_2$ | Hydrogen | 62.71 vol % |
| CO | Carbon Monoxide | 18.57 |
| $CO_2$ | Carbon Dioxide | 10.67 |
| $CH_4$ | Methane | 7.58 |
| $C_2H_6$ | Ethane | 0.48 |
| $C_3$ TO $C_6$ | Propane through hexane | <0.01 |
| $C_6H_6$ | Benzene | <17 ppm |
| COS | Carbonyl Sulfide | 4 ppm |
| $CS_2$ | Carbon Disulfide | 0.05 ppm |
| $H_2S$ | Hydrogen Sulfide | <5 ppm |
| $C_{10}H_8$ | Naphthalene | 2.6 ppb |
| $C_{10}H_7CH_3$ | 2-Methylnaphthalene | ~0.6 ppb |
| $C_{12}H_8$ | Acenaphthalene | ~0.4 ppb |
| $C_{12}H_8O$ | Dibenzofuran | 0.36 ppb |
| PCDF + PCDD | Polychlorinated-dibenzofurans + Dioxins | 0.0041 ppt TEQ |

What has been found experimentally was that the syngas included hydrogen and carbon monoxide. For fuel cells the key poisons, such as carbonyl sulfide, hydrogen sulfide, carbon disulfide, hydrogen chloride, and polychlorinated organics were identified. For Fischer-Tropsch, methanol synthesis, methanation, etc., this syngas is acceptable. However, to make the process more efficient and environmentally desirable, the side products, such as $CH_4$ and $CO_2$ need to be used and not released to the atmosphere. These are also the side products of FT that are called "tail gases." Yet other aspects of some embodiments of the present invention include using these side species of $CH_4$ and $CO_2$ through recycle back to the front end of the process, such as through a rotary reformer.

Another aspect of power recovery is to reduce the energy losses of a waste-reforming kiln. One consideration is that some kilns are operated at a high temperature, followed by an even higher temperature steam/$CO_2$ reformer which is then followed by the desulfurizer and high temperature filter—all energy-inefficient from heat losses from the process units themselves and from the complex of hot process piping.

Regarding Fischer-Tropsch, one aspect according to some embodiments is to develop a process train where the Fischer-Tropsch unit could produce enough high carbon product, such as fertilizer and as high density, unsaturated paraffin wax containing little hydrogen, so that the carbon in the waste feed would be sequestered in this product, without significant carbon emissions leaving the process anywhere else. The Fischer-Tropsch train also should produce steam for a steam-turbo-generator to make electricity for the process plant.

SUMMARY OF THE INVENTION

Various embodiments of the present invention relate to a power recovery process in waste steam/$CO_2$ reformers whereby a waste stream can release energy without having to burn the waste or the syngas and consume oxygen and have large carbon dioxide emissions.

Various embodiments do not make use of fuel cells as its critical component but makes use of highly exothermic chemical reactors using syngas to produce large amounts of heat, such as by Fischer-Tropsch reactions.

Some embodiments relate to control or elimination of the emissions of greenhouse gases in the power recovery process of this invention with the goal of producing energy in the future carbonless world economy.

Further, yet other embodiments show how to eliminate the typical light gas discharge from Fischer-Tropsch, shift converters, pressure swing adsorber, membrane systems, etc. by recycling back to the kiln as a "recycling to extinction," because the steam reforming chemistry breaks apart these light gases into their elemental constituents.

One aspect of some embodiments include a process train for power recovery with an improved duplex kiln in a recycle way that combines the functions of the conventional kiln, steam/$CO_2$ reformer, and the high temperature filter into a single unit. The desulfurizer/getter bed can operate at a lower temperature and can follow the duplex kiln.

Further embodiments involve using the above duplex kiln and getter bed in a process train that includes a heat exchanger/steam superheater are disclosed that will rapidly quench-cool the syngas down from 300 to 500° C. (600 to 900° F.) temperature range of the desulfurizer to 150° C. (300° F.). The concept here is to rapidly quench the syngas so that the undesirable heavy hydrocarbon recombination reactions (i.e. "De-Novo") that make dioxins and furans do not have time to form, since they are kinetically limited. These recombination reactions involve multi-step polymerization &/or ring formation and are slowed as the temperatures are lowered.

In still further embodiments the Brayton cycle turbine is used to recover energy from the high temperature gas, while cooling it for feeding to both the Fischer-Tropsch unit to produce the high-carbon content product for sequestering the carbon and the shift converter and pressure-swing absorber to produce hydrogen fuel.

As an alternative embodiment, a conventional indirectly fired, calcining kiln can be used where the very hot syngas exiting from the steam reformer can heat carbon dioxide gas or air to supply the indirect heat to the kiln to take over from the natural gas burners commonly used.

The Fischer-Tropsch reactor, as discussed above, is highly exothermic and produces high quality steam for operating a conventional steam turbo-generator system for powering the plant.

Various embodiments of the present invention pertain to the conversion of a waste stream by steam/$CO_2$ reforming to produce a syngas that is used in a Fischer-Tropsch reactor as well as its tail gas recycle back to the front end to produce energy and sequester the carbon of the waste at the same time.

Yet other embodiments replace the Fischer-Tropsch reactor with other highly exothermic reactors that produce a high-carbon content product for sequestering carbon and produce large amounts of energy, and use recycle to advantage, and also interchanging the syngas cleaning process units around while keeping the same functionality are covered under this invention. All such generalizations are covered by this invention.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

DETAILED DESCRIPTION OF THE PREFERRED EMBODIMENTS

Figure 1:
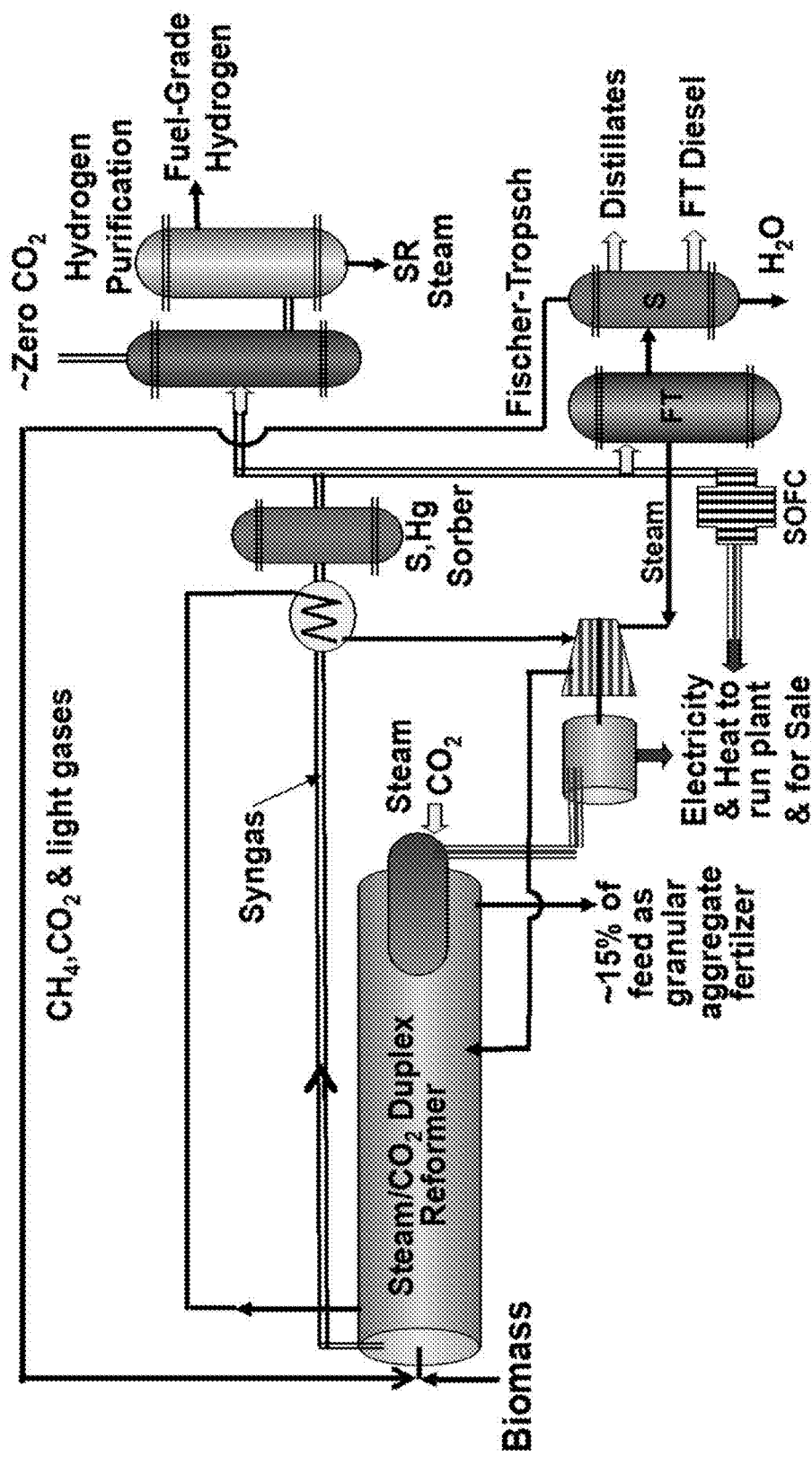
FIG. 1: Schematic graphic of a process according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that the features 1020.1 and 20.1 may be backward compatible, such that a feature (NXX.XX) may include features compatible with other various embodiments (MXX.XX), as would be understood by those of ordinary skill in the art. This description convention also applies to the use of prime ('), double prime ("), and triple prime ('") suffix element numbers. Therefore, it is not necessary to describe the features of 20.1, 20.1', 20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests or simulations that were performed. It is understood that such examples are by way of example only, and are not to be construed as being limitations on any embodiment of the present invention. Further, it is understood that embodiments of the present invention are not necessarily limited to or described by the mathematical analysis presented herein.

Various references may be made to one or more processes, algorithms, operational methods, or logic, accompanied by a diagram showing such organized in a particular sequence. It is understood that the order of such a sequence is by example only, and is not intended to be limiting on any embodiment of the invention.

What will be shown and described herein are one or more functional relationships among variables. Specific nomenclature for the variables may be provided, although some relationships may include variables that will be recognized by persons of ordinary skill in the art for their meaning. For example, "t" could be representative of temperature or time, as would be readily apparent by their usage. However, it is further recognized that such functional relationships can be expressed in a variety of equivalents using standard techniques of mathematical analysis (for instance, the relationship F=ma is equivalent to the relationship F/a=m). Further, in those embodiments in which functional relationships are implemented in an algorithm or computer software, it is understood that an algorithm-implemented variable can correspond to a variable shown herein, with this correspondence including a scaling factor, control system gain, noise filter, or the like.

Figure 12A:
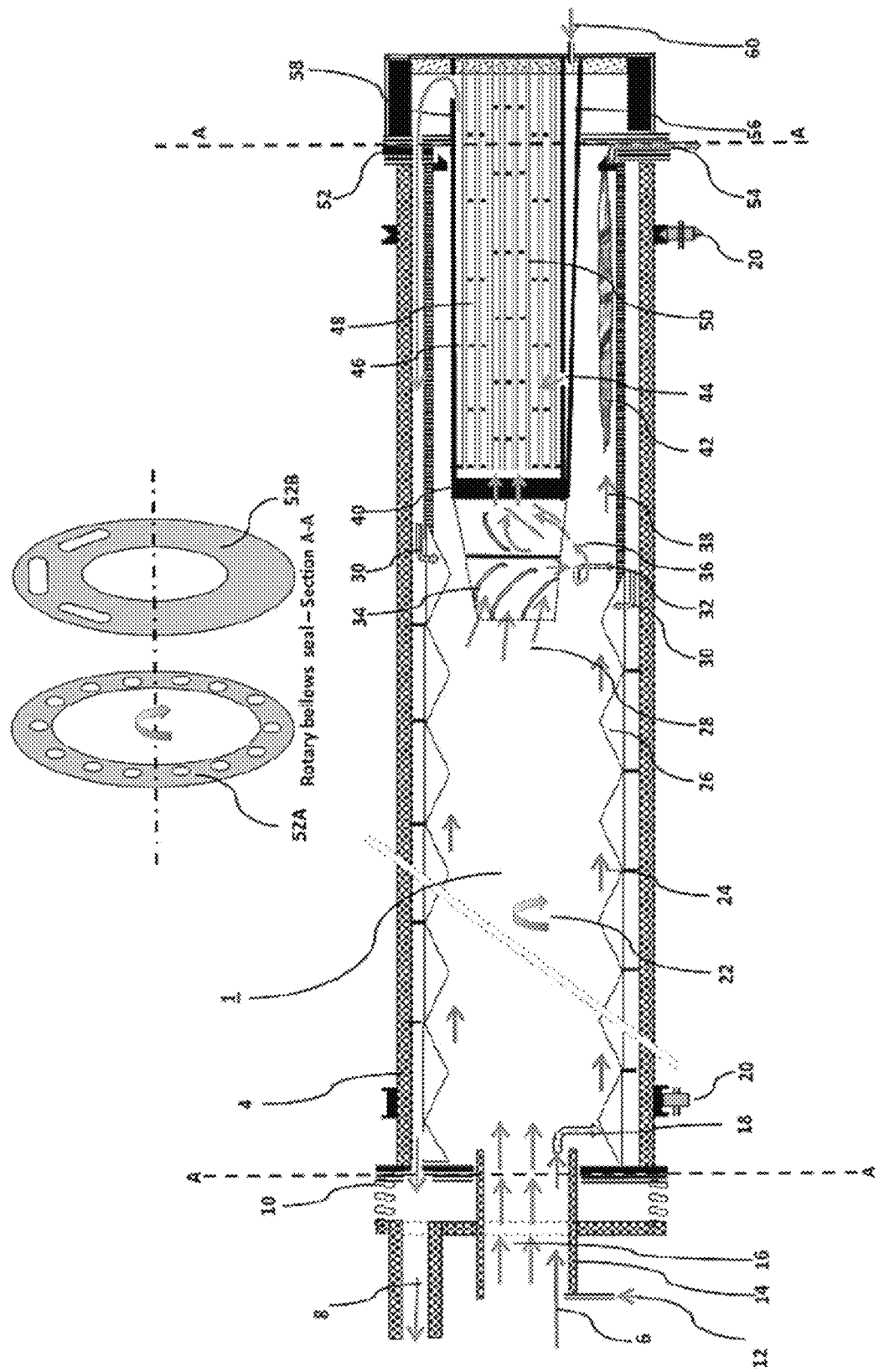
FIG. 12A is a cross sectional view of a rotary steam and carbon dioxide reformer as used in some embodiments of the present invention.
Figure 12B:
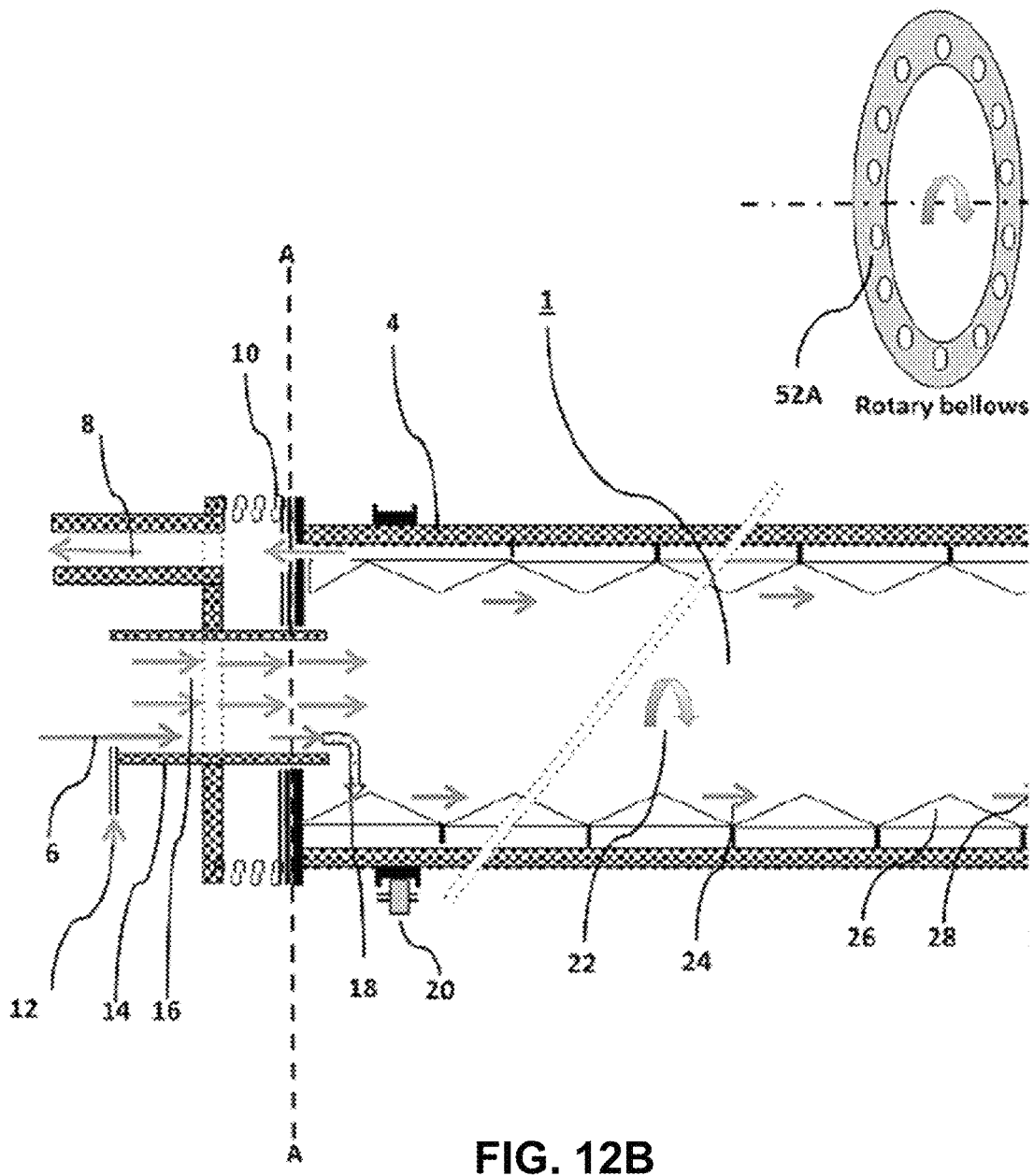
FIG. 12B is a portion of the cross sectional view of FIG. 8A.
Figure 12C:
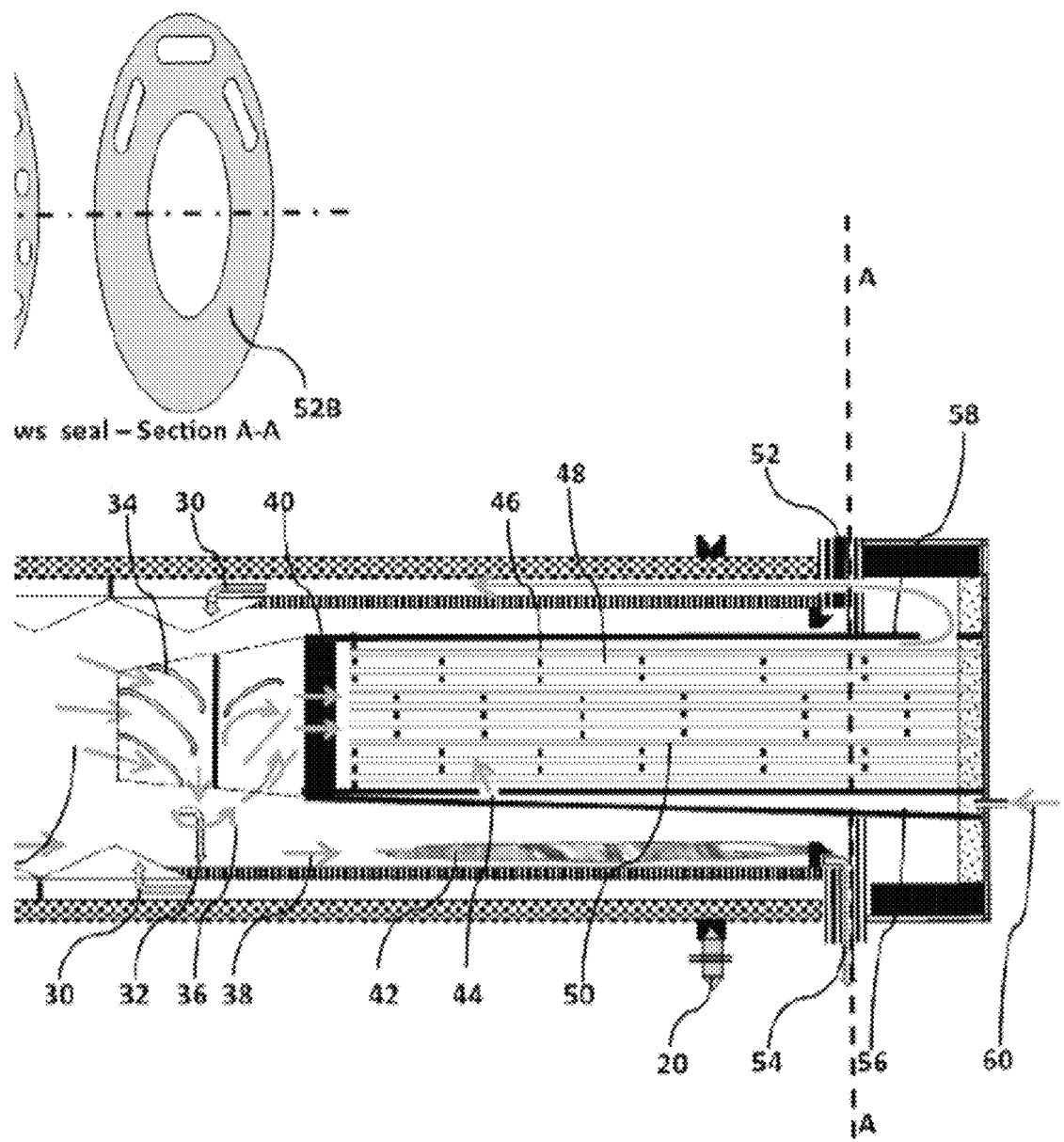
FIG. 12C is a portion of the cross sectional view of FIG. 8A.

This application incorporates by reference U.S. patent application Ser. No. 14/847,798, filed Sep. 8, 2015, titled PROCESS AND SYSTEM FOR DUPLEX ROTARY REFORMER, incorporated with regards to operation, components, and other aspects of the reformer shown in FIGS. 12A, 12B, and 12C.

In FIG. 1, there is shown one embodiment of an improved duplex kiln system 1000 that combines the functions of the conventional kiln, steam/$CO_2$ reformer, and the high temperature filter into a single unit. In FIG. 1, is shown how the new concept of a duplex kiln can be followed by a desulfurizer/getter bed, quench heat exchanger for provided superheated steam for the duplex kiln, and the Brayton turbine for generating power by cooling the syngas, which is then fed to both a Fischer-Tropsch reactor and Shift/Pressure Swing Absorption System.

Figure 2:
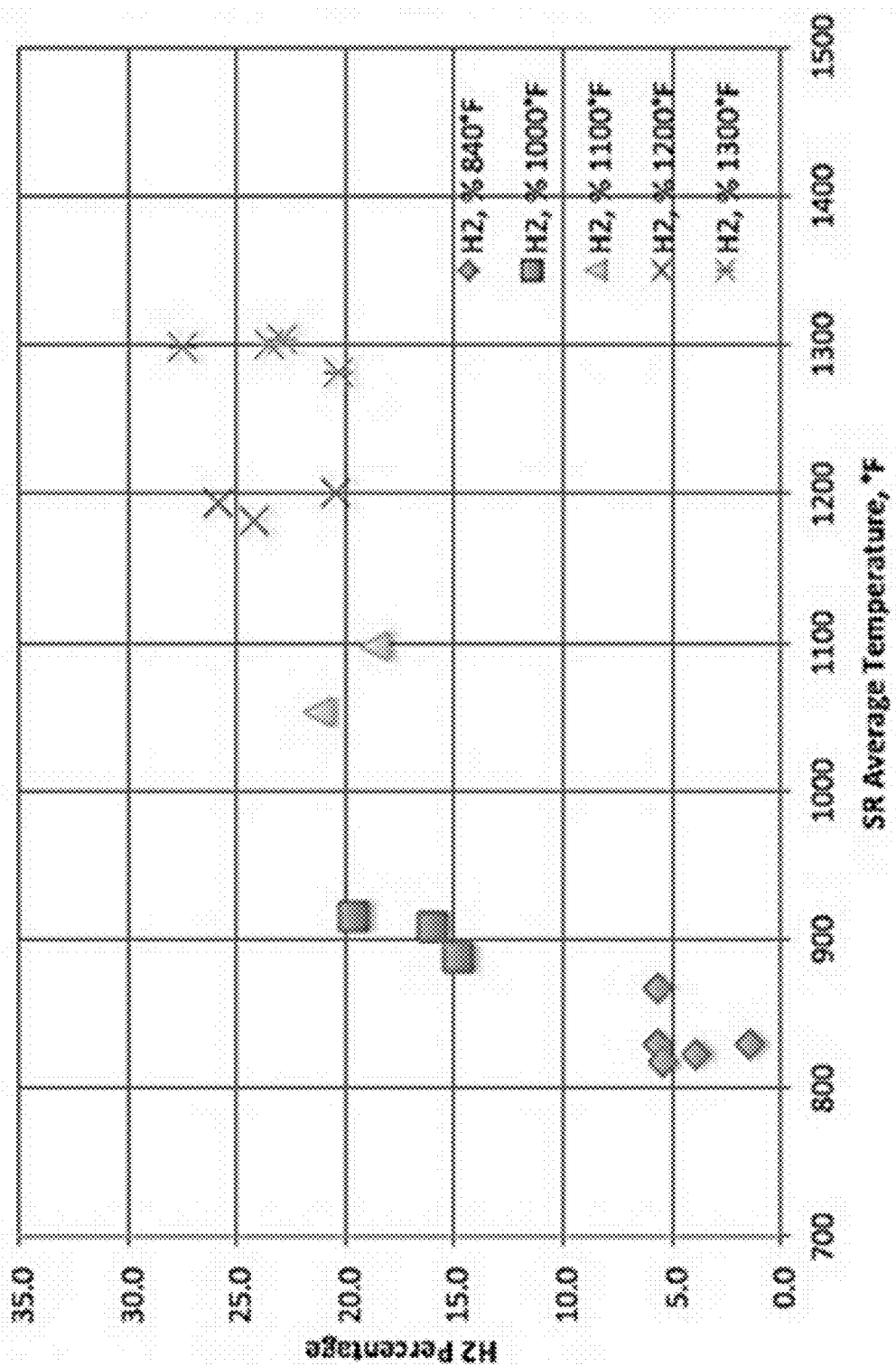
FIG. 2: Plot of hydrogen percentage verses SR temperature as produced in a method according to one embodiment of the present invention.
Figure 3:
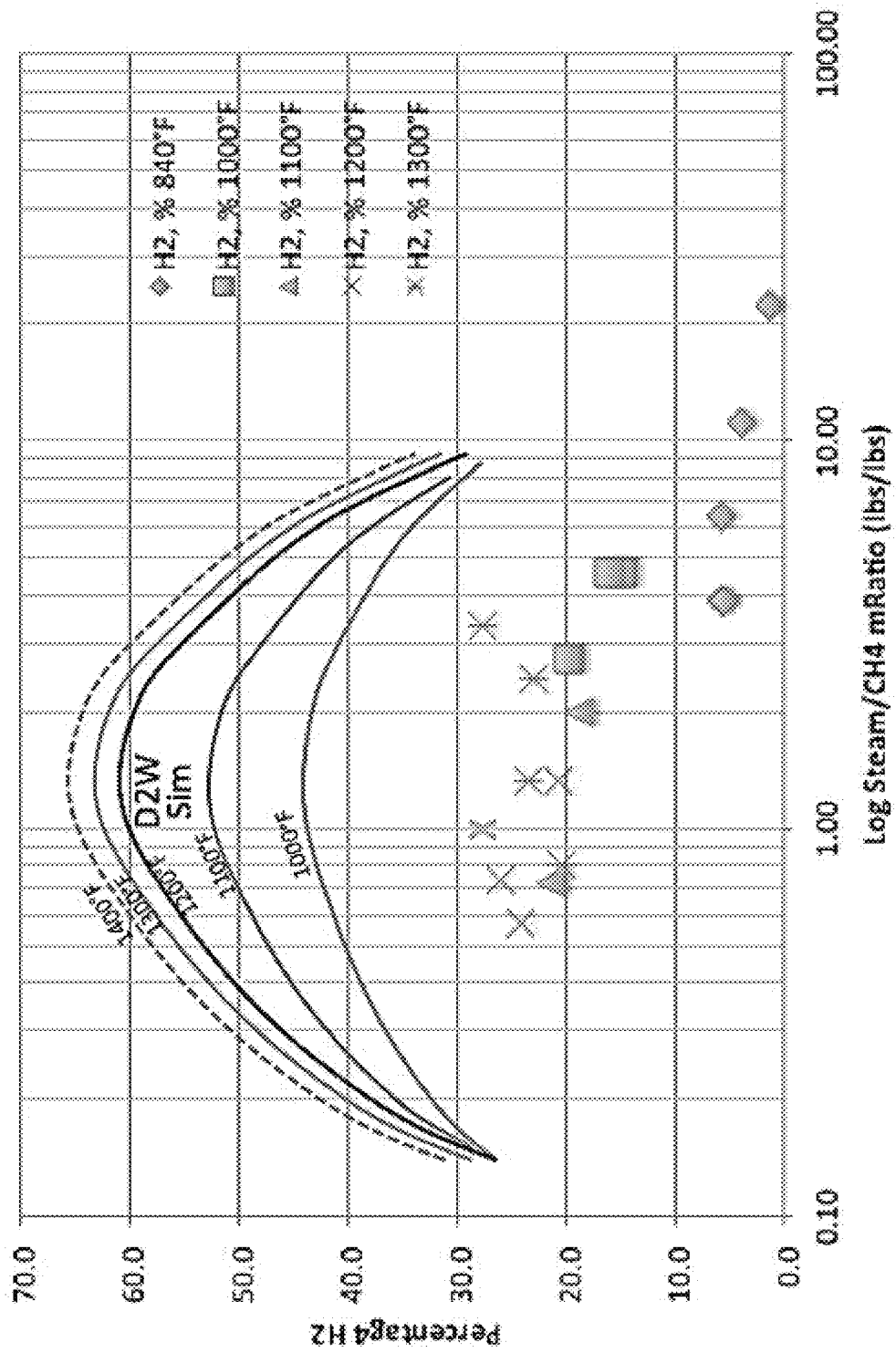
FIG. 3: Log plot of $H_2$ vs steam/CH4 mass ratio as produced in a method according to one embodiment of the present invention.
Figure 4:
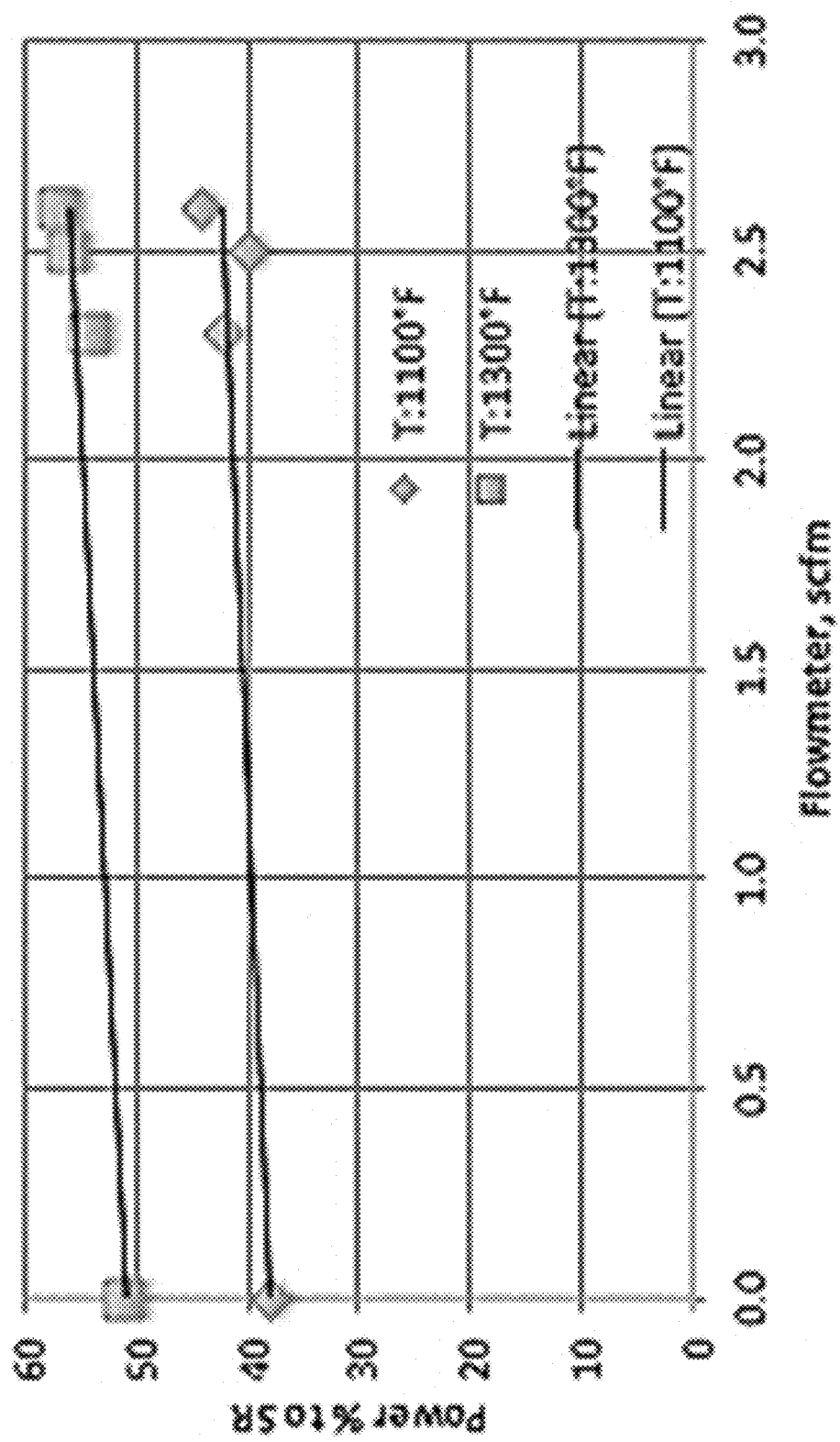
FIG. 4: Power consumption in recycle mode as produced in a method according to one embodiment of the present invention.
Figure 5:
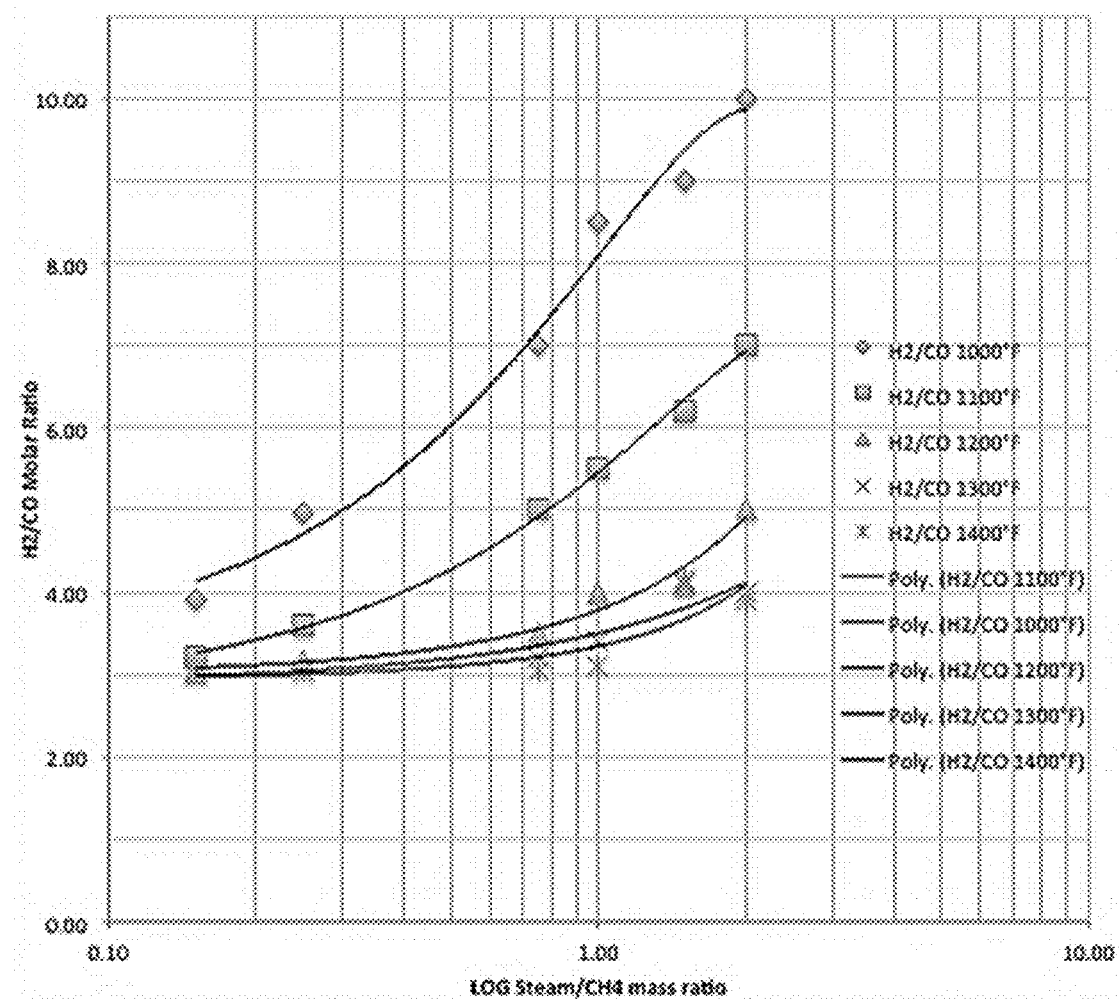
FIG. 5: Effect of recycle mode on H2/CO ratio as produced in a method according to one embodiment of the present invention.
Figure 6:
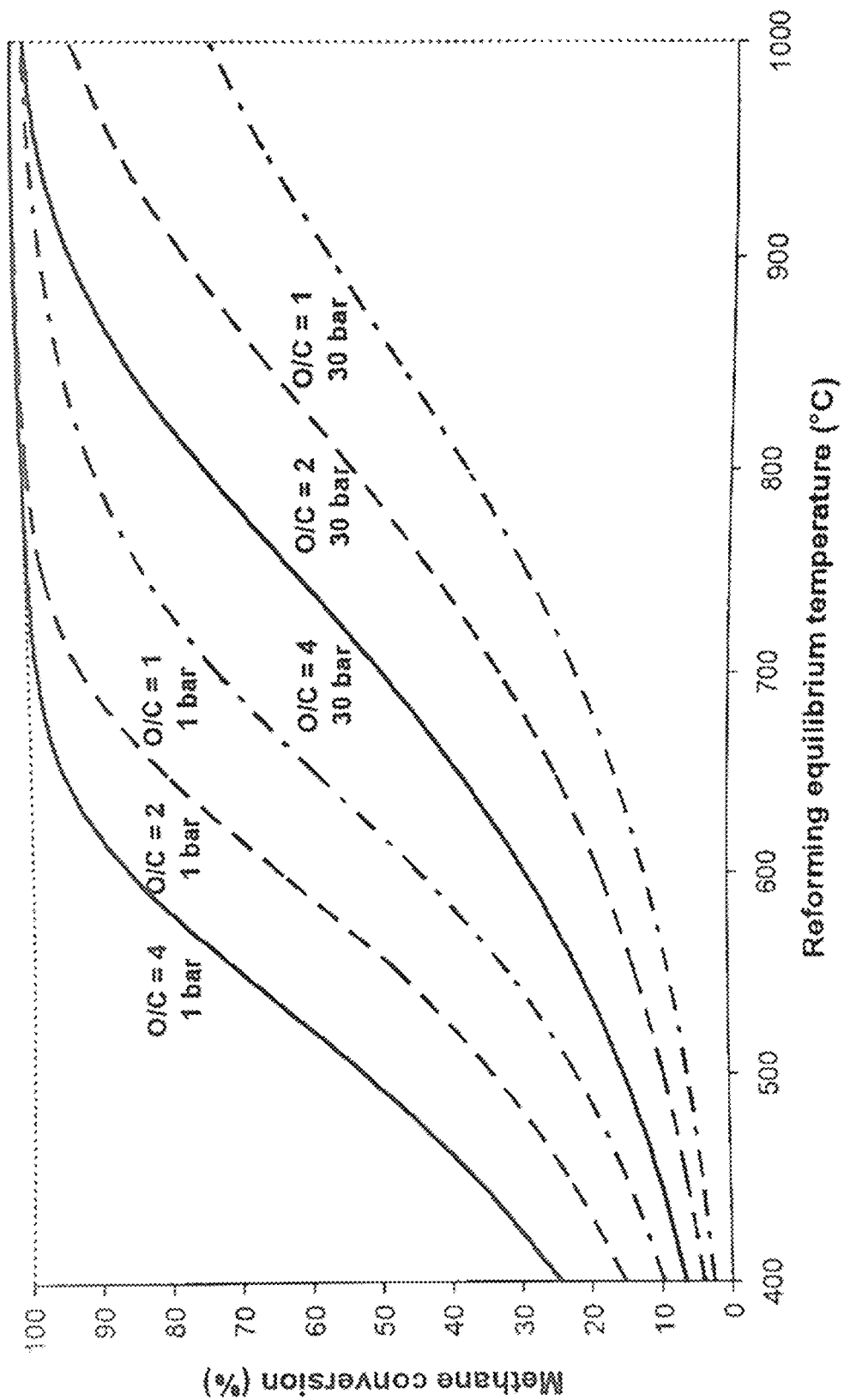
FIG. 6: Predictions of H2/CO ratio as produced in a method according to one embodiment of the present invention.
Figure 7:
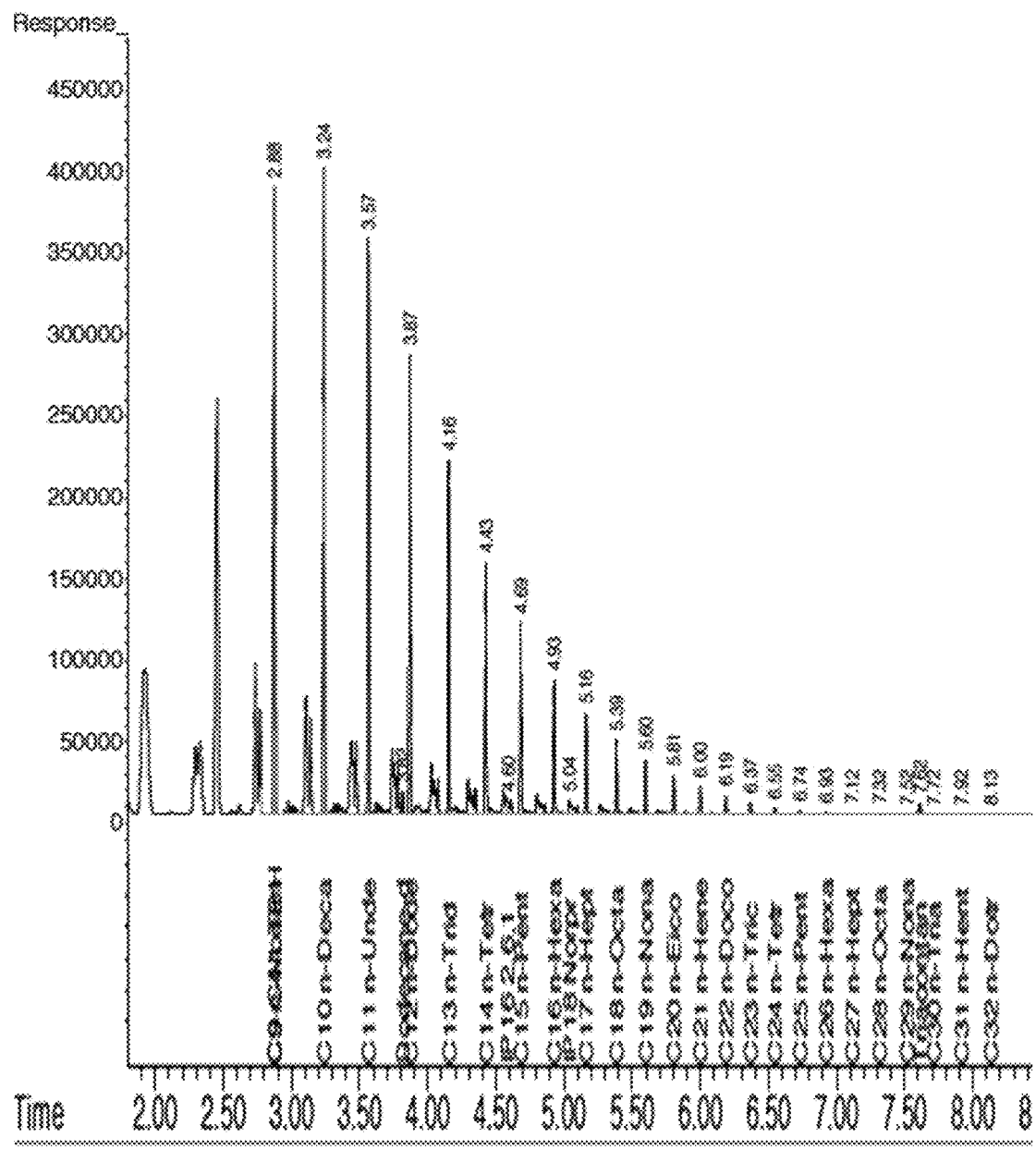
FIG. 7: FT liquids produced with a catalyst on finned tube as produced in a method according to one embodiment of the present invention.
Figure 8:
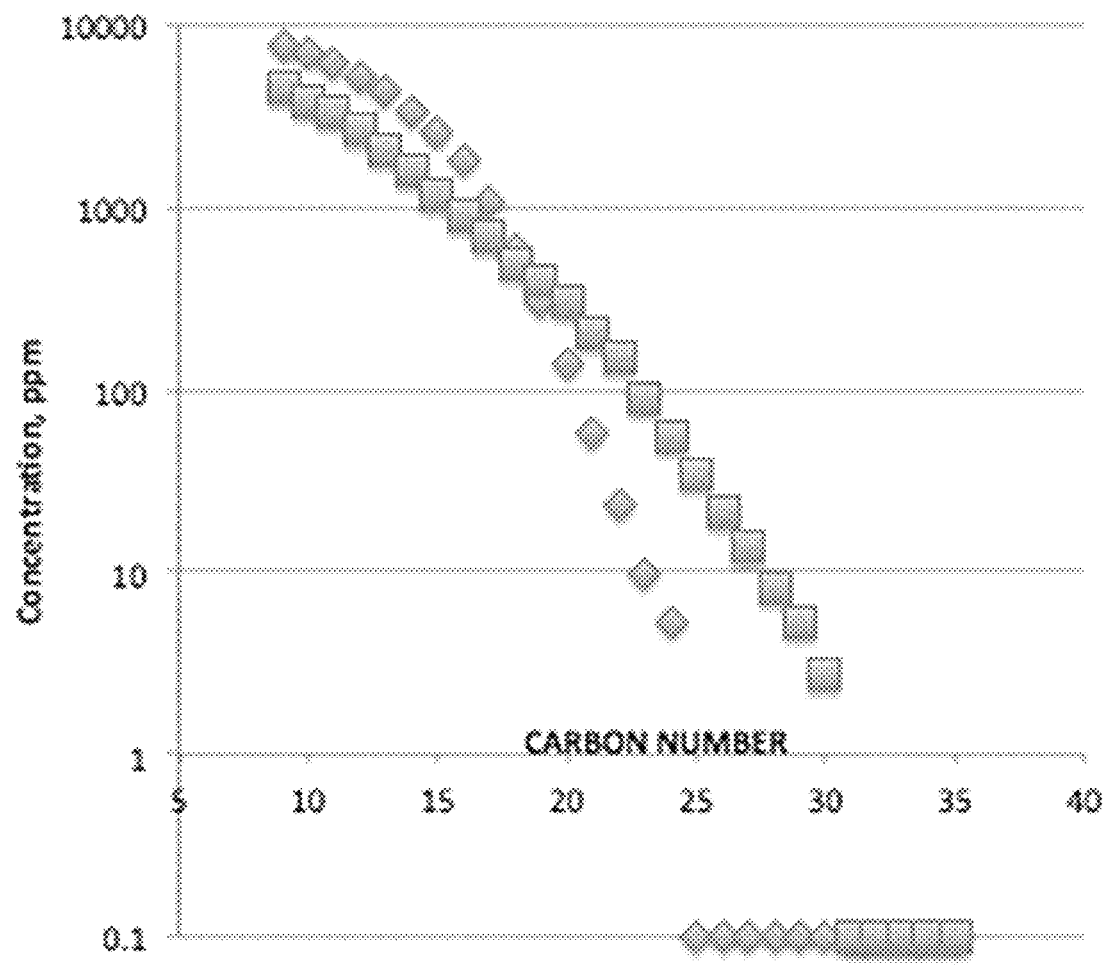
FIG. 8: FT liquid carbon number distribution produced by our catalyst on finned tubes at two pressures: Red squares at 250 PSIG and blue diamonds at 125 psig as produced in a method according to one embodiment of the present invention.

FIG. 2 shows the effect of temperature. In FIG. 3 is shown the effect of steam/$CH_4$ ratio. FIGS. 4 and 5 shows the effects of recycle. FIG. 6 shows the comparison with published effects of steam/$CH_4$ ratio. FIGS. 7 and 8 shows the advantage of using a Fischer-Tropsch process of two units that make the high-carbon product, make steam and accomplishes sequestration carbon balance in capturing nearly all of the carbon dioxide emissions. In FIG. 8 it is shown how the Fischer-Tropsch process that makes paraffin wax product for carbon sequestration accomplishes recycling the light hydrocarbons consisting of methane, ethane, ethylene, propane, etc. to avoid their emissions as powerful greenhouse gases (i.e. methane) and also recycling the lighter hydrocarbons to help maintain a higher $H_2$/CO ratio of the syngas. It also describes how a waste stream can be made to release energy without having to burn the waste or the syngas. At the same time the waste can be converted into use carbon-containing fertilizer, hydrogen fuel, and a carbon-sequestering, high-carbon content product of commercial value, such as unsaturated, high-density paraffin wax.

FIG. 6 shows the use of a conventional indirectly fired, calcining kiln where the very hot syngas exiting from the steam reformer can heat carbon dioxide gas or air to supply the indirect heat to the kiln to take over from the natural gas burners commonly used. Or this heat from heat exchanger 114, can be used to heat the recycle gas stream 116. These two methods of heat integration can be used in combination as well.

The purpose of the following experimental work was to determine various ways in which to react the $CH_4$ and $CO_2$ to get useful syngas, and preferably avoid the release of the $CH_4$ and $CO_2$ to the atmosphere.

One operational aspect of the operation and maintenance cost of the full size unit is the steam/$CO_2$ reformer (SR) operating temperature used to obtain a high quality syngas at the proper $H_2$/CO ratio in the range of 1,200-1,400° F. FIG. 2 shows the temperature results to date reaching the 27% $H_2$ goal. Experimental data herein show that $H_2$/CO=2.11±0.5 was measured.

One economic benefit is obtained from operating at the lowest steam/$CO_2$ reformer temperature and the lowest superheated steam addition to achieve the required FT $H_2$/CO ratio. An analysis using the mass ratio of steam to methane is shown as a log plot is shown in FIG. 3.

One useful steam and $CH_4$ mixture appears to be a ratio of about 1.1. The curved lines at the upper left show the results of different temperature D2W simulations involving Gibbs Free Energy Minimization. They all show the temperature effect and show clear maxima at each temperature. The strongest temperature increase appears to at 1.1 Steam/$CH_4$ mass ratio. Thus, a slight 10% excess of steam is indicted as optimal. Blue data symbols points are pilot data.

The percentage $CH_4$ conversion comparing theoretical equilibrium composition to experimental non-catalytic conversion achieved in our Steam/$CO_2$ reactor design is about 48%. This arises from equilibrium is the maximum ideal conversion without any kinetic limitations.

Figure 10:
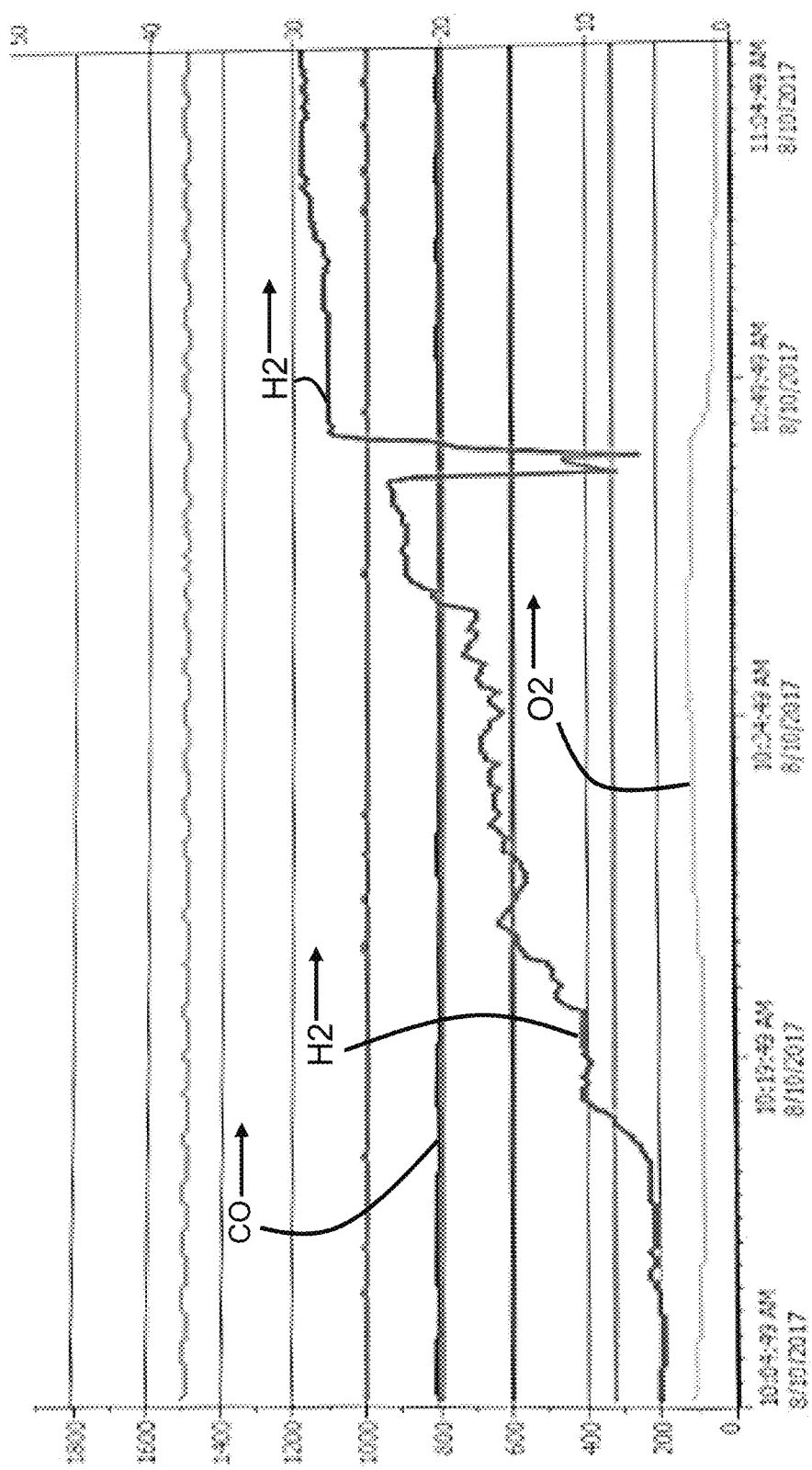
FIG. 10: Peak H2 production at near feed capacity as produced in a method according to one embodiment of the present invention.

One possible conclusion is that recycle mode had a negligible effect on the $H_2$ production, as shown in the D2W simulation results shown in FIG. 10 and the two data points using recycle of FIG. 7 at $H_2$ levels of 21-24% and Steam/$CH_4$ ratio around 1.4. They are in line with other non-recycle mode data points. The $H_2$ production of 0.135 lb. moles/hr. is about the same as the flow configuration without use of a blower. One aspect of the recycle mode is to produce pressure stability and make operation easier and simpler for automatic control. A possible advantage of recycle mode is that it consumes a small increase in power, as shown in FIG. 4.

The effect of steam/$CH_4$ ratio and temperature is confirmed by predictions as shown in FIG. 6. This data shows why it is useful in operating the main steam/$CO_2$ reactor at high temperature such as over 1500° F. (813° C.) to obtain the $CH_4$ conversion over 92%.

The analytical laboratory work was done on two samples, the first was run at 250 psig and second at 125 psig.

The analysis included the extraction of the chromatogram for the 10× dilution run to get a better sense of the statement below about the fingerprint. The (likely) C8 peak is just before the 2.88 min retention time peak (C9), and is appropriately positioned with an expected relative retention time (looks like C8). The other stuff is unknown, since this technique (GC-FID) does not have ability to explore mass detection, but it could be a mix of other light organics with lower responses by FID (i.e. PAHs), or maybe olefins.

FIG. 7: Shows the GC/FID Chromatogram for the FT Liquids produced by our catalyst on finned tubes at two pressures. The sharp narrow peaks are the laboratory standards and the lower and wider peaks are the results for our FT liquids. The variety of peaks at the left of C8, are lighter compounds discussed above.

FIG. 8: shows the FT liquid Carbon number distribution produced by the catalyst on finned tubes at two pressures: 125 psig as blue diamonds and 250 psig at red squares. The results are graphically displayed as a log scale. As can be seen, the pressure has an effect in shifting the fractions of naphthas, kerosenes, diesel, and wax fractions. For small size FT process skids, it is possible that better economics are realized at the lower pressures.

Referring to FIG. 12, the functionality of the embodiment of FIG. 12 is combined into a single kiln to increase the thermal efficiency and reduce the cost. This design is referred to as the Duplex Kiln, 1, that in some embodiments combines the functions of the conventional kiln, steam/$CO_2$ reformer, swirl fines drop out, the high temperature filter, recover of high temperature radial heat loss, heating internal heating of helical spiral flights at the wall into a single unit.

Referring to the duplex kiln 1 in FIG. 12, the waste stream 6 is fed oxygen-free through the large entry pipe 14 combined with recycle light gases through pipe 12. This entry region remains stationary whereas the kiln tube wall, 4, rotates as shown by arrow 22 and is sealed by means of a pair of bellows tensioned rotary plates, 10, where in the bellows applies pressure to the pair of rotating sealing plates, 52A at the left and 52B at the left which rotates with the tube 4 powered by drive pinion gear 20. Note that the bellows 10 is at the cold end of the duplex reformer where this bellows will have longer life. The thermal expansion is about 5" typically and the bellows can accommodate this movement, as well as the wide pinion drive gears. At the hot end of the duplex reformer the drive pinion is in a V-shaped gear arrangement to handle the end thrust from thermal expansion. As the waste enters tube 14, the gaseous portion moves above the waste into the kiln as gas stream 16. Once inside the kiln rotating tube 4, the solids are dropped into the bottom of kiln by chute 18. The waste solids 6 drop by this chute 18 onto the moving helical spiral flights 26 moving from left to right and carrying with them the waste 24. These helical spiral flights 26 are hollow with the gas flowing, 30, in their interior from right to left, counter-current to the waste and leaving through gas exit tube 8.

Again referring to FIG. 12, as the waste 24 is moved progressively to the right by the helical spiral flights 24 if eventually enters a flat wall region 38 where there is a tumbling media 42 that helps break lumps of waste and helps form an aggregate material that leaves the rotary kiln through chute 54.

Further referring to FIG. 12, the gases 16 enter the swirl region 36 where their flow trajectory is driven into a curved flow by vanes 34. In this region 36 the curved flow trajectory velocity throws the particles downward as shown by arrow 32. For their these gases with less fines pass through porous media filter 40 and enter the electrical heated reactor 48 that has interior disk and donut baffles 46 which steer the flow to pass cross flow around the cylindrical heating elements 50 for convective heat transfer. This reactor 48 does not rotate as it is fixed to the stationary region of the kiln by fixes cylindrical structure 58 that is attached to the cylindrical, insulated cap 52 The hole pattern allows the finished syngas 30 to enter the helical spiral flights 26 and leave this duplex kiln at exit pipe 8. This electrically heated reactor 48 is further supported mechanically by hollow truss 56 through which superheated steam and optionally added $CO_2$ if fed by port 60 and enters this reactor through port 44. This added reactant gases help further drive the formation of the finished syngas for substantial conversion to thermodynamically equilibrium with an internal residence time at temperature of around 1.5 seconds.

Figure 13:
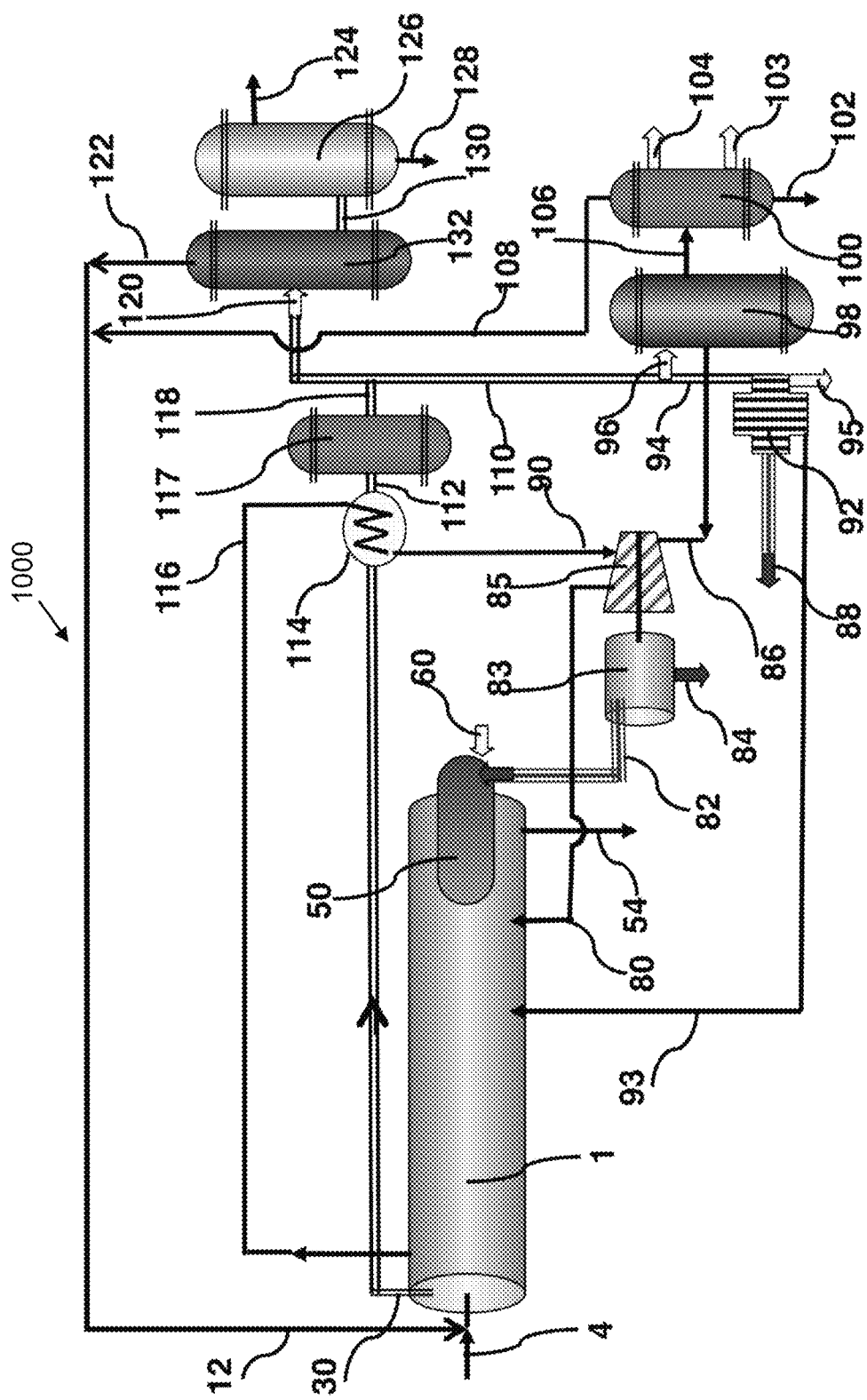
FIG. 13: Placement of stream/CO2 duplex rotary reformer into a process according to one embodiment of the present invention, and also the system 100 of FIG. 1.

In FIG. 13 the duplex rotary steam/$CO_2$ reformer 1 is shown in an embodiment of the waste-to-fuel and energy process design. This shows the concept of the rotary reformer with an integral steam reformer at the exit end which eliminates some high temperature piping and the heat losses associated with such piping. The biomass/waste feedstock 4 enters the process around room temperature at the left. The finished syngas 30 produced leaves at the left at somewhat above room temperature. The solid biomass/waste enters at the left and is mixed together with warm light end gases 12 from the downstream process units, such as gas 108 from Fischer-Tropsch and/or PSA offgases 122 from the hydrogen purification section shown as process steps 126 and 132.

Now referring to the exit end to the right of the duplex rotary steam/$CO_2$ reformer 1, the electrically heated, hot gas-phase main steam/$CO_2$ reformer 50 is inserted though the right side. Any inorganics and solid carbon phases leave the duplex rotary reformer warm through exit pipe 54 that is configured to eliminate any entry of outside air. Besides the electrical heating, there are optionally two other means of supplying the endothermic heat needed to drive the steam/$CO_2$ reforming chemistry: [1] warm recycled light end gases 12 as well as hot power generation hot gases 80 from Brayton cycle heat engine and 93 from hot cathode nitrogen-rich off-gases. This hot gas heat enters the reformer 1 into the typical oven that surrounds commercial kiln retort tubes that rotate, and these gases do not enter with the recycled gases 12 that enter the process flow which is preferably oxygen-free. Hot fuel cell anode off-gases 95 containing unreacted $H_2$ and CO plus $CO_2$ and light hydrocarbons are mixed into 60 to enter the electrically heated steam/$CO_2$ reformer.

Referring to FIG. 13, the finished syngas 30 from the duplex rotary reformer, 1 is next heated by heat exchanger 114 using waste heat 116 from the duplex reformer 1, so that the hot syngas 112 enters the absorber clean-up beds 117 for sulfur, mercury, chlorine, etc. removal. The cleaned, finished syngas 118 is now ready for use in product production of fuels, hydrogen and power. This clean syngas 120 first enters the Shift Converter 132, then enriched with $H_2$ in steam 130 enters the PSA 126 for concentrating the hydrogen. Offgases 122 from the Shift Converter are recycled back 12 to the front end of the duplex reformer. The PSA produces renewable hydrogen fuel, 124. There is also an optional steam stream 128 that can be used in stream 60 to assist the electrically-heated reformer 50.

Additionally in FIG. 13, this syngas 188 can be sent via 110 down to the Fischer-Tropsch (FT) where it enters via 96 into the FT reactor 98 that produces the crude paraffinic hydrogen fuel 106. This FT reactor 98 is highly exothermic and produces large quantities of high pressure steam that can be used in the Brayton cycle turbine/engine 85 to make electrical power 82 via generator 83. The hot turbine off gases 80 can be used to heat the duplex reformer. The crude FT paraffinic fuel 106 is separated and distilled in unit 100 into a naphthenic fuel, like, JET, 104 and into FT Diesel No. 2 103, both of which can be sold. The off-spec streams 102 consisting mostly of wax and alcohols and steam can be used in stream 60 for further reforming in the electrically heated steam/$CO_2$ reformer 50 to make more syngas and eventually more product.

In FIG. 13, the clean syngas remaining 94 enters a solid oxide fuel cell 92 that converts electrochemically this syngas into electricity and power 88 to drive the plant and also start up the plant when the fuel cell is run on natural gas or tank propane or diesel. This fuel cell 92 anodically reacts some 85% of the syngas and the 15% left over gas consisting of unreacted $H_2$ and CO plus $CO_2$ can be used in stream 60. The cathode off-gas consists of hot nitrogen and this can be used to further heat the duplex reformer via stream 93.

Some embodiments of the present invention provide thermal efficiency derived from inside of the rotary reformer (commercial calciner equipment) with the inserted spiral flights that are hollow and allow the hot syngas to be counter-flowed from the right back out the entry through the rotary plate seal. This provides the heat for the solids feed and cools the syngas as well. In the center is a cyclonic swirl vane section that helps drop out fine solids entrained in the gas. The fines drop into the inorganic solids left after initial steam reforming around 900-1100° F. The cleaned syngas passes through a mesh filter and enter the high temperature main steam/$CO_2$ reformer that is electrically heated. The hot syngas at 1800-2000° F. that exits is rich in hydrogen, as shown in Table 1. This hot finished syngas is then passed through the spiral flights in counterflow direction to exit cooled at the entry port of the rotary reformer. This is generally about 15 wt % of the feedstock entering the process. Carbon efficiency is achieved via the bottom exit there is also the option of a rebar section that tumbles to break up any larger pieces of solids into an aggregate size the material that can be used as a 70-80% carbon rich 0-10-10 slow release pellet fertilizer, thus sequestering this carbon in the ground and not resulting the release of GHG to the Earth's atmosphere.

Next a number of examples are given according to various embodiments of the present invention:

Example #1

Using the empirical formula for typical municipal solid waste, MSW, we show two reactions: first the conventional steam reforming using a stoichiometric amount of steam to make just CO and $H_2$.

MSW and Stoichiometric Steam:

$$C_1H_{1.67}O_{0.47} + 0.53H_2O \rightarrow CO + 1.36H_2$$

In this case 1 kg of waste will yield 1.45 kg of syngas.

Example #2: Superstoichiometric in $CO_2$ and $C_2H_4$

By contrast, here is one improved reforming reaction which involves a substoichiometric amount of steam but has the light hydrocarbon Fischer-Tropsch and shift/PSA overhead represented for simplicity by C2H4, plus $CO_2$ and $H_2$, added.

$$C_1H_{1.67}O_{0.47} + 0.55C_2H_4 + 0.69H_2 + 1.5CO_2 + 0.04H_2O \rightarrow 3.68CO + 2.67H_2 \quad [1]$$

In this case, 1 kg of waste will yield 5.11 kg of syngas, which is a 350% increase in the mass of syngas product formed from a given mass of waste.

This achieves the formation only of CO and $H_2$, and thus is stoichiometric which respect to the combination of steam plus $CO_2$ plus $C_2H_4$. Thus, less steam (i.e substoichiometric) is required and greenhouse-problematic light hydrocarbons and $CO_2$ can be used in large amounts to achieve overall the stoichiometric conversion to syngas desired with a preferred $H_2/CO$ ratio around 0.73. The products $CH_4$, $C_3H_8$ or other light hydrocarbons are actually involved in the real world in combination with $C_2H_4$ shown in the reaction. In a typical Fischer-Tropsch process all of these light hydrocarbons are formed and would be in the recycle. Thus, the use of Fischer-Tropsch is simplified in some embodiments. The $CH_4$ is produced as a part of the waste light gases coming off the tops of the Fischer-Tropsch gravity separator. Preferably, no distillation is required. Any other light gases that are also carried along with the waste $CH_4$ can go back to the steam reformer as well.

In some embodiments it is economic to recycle 100% of the $CO_2$ and whatever optimum amount of $CH_4$ from Fischer-Tropsch to make the whole system balance, sequestering all of the $CO_2$ while making useful paraffin wax that is high in carbon content, high in commercial value, and not burned in its lifecycle. So in FIG. 13 the Improved Carbon Sequestration can be accomplished as shown by the carbon balance. Thus, by adjusting the carbon in the Shift/PSA recycle 86 plus the carbon in the Fischer-Tropsch overhead recycle 108, the carbon in the waste 100 is made to just equal the carbon in the Fischer-Tropsch product, paraffin wax 102. So what could be accomplished in some embodiments is the sequestration of the carbon in the waste by the formation of the high carbon content paraffin wax. Yet other embodiments of the present invention contemplate other Fischer-Tropsch-like processes that can be selected that will accomplish this total carbon sequestration. Commercially, there may be be an economic optimum situation where one may not want to sequester all of the carbon in the waste, but this example shows that this is possible.

Alternatively, the reactor in FIG. 13 can consist of a conventional shell and tube heat exchanger with the pellets of catalyst in the tubes and the liquid phase in the shell. To avoid temperature hot spots in the tubes, the ratio of catalyst diameter to tube diameter shall preferably be more than about one to five.

Figure 14:
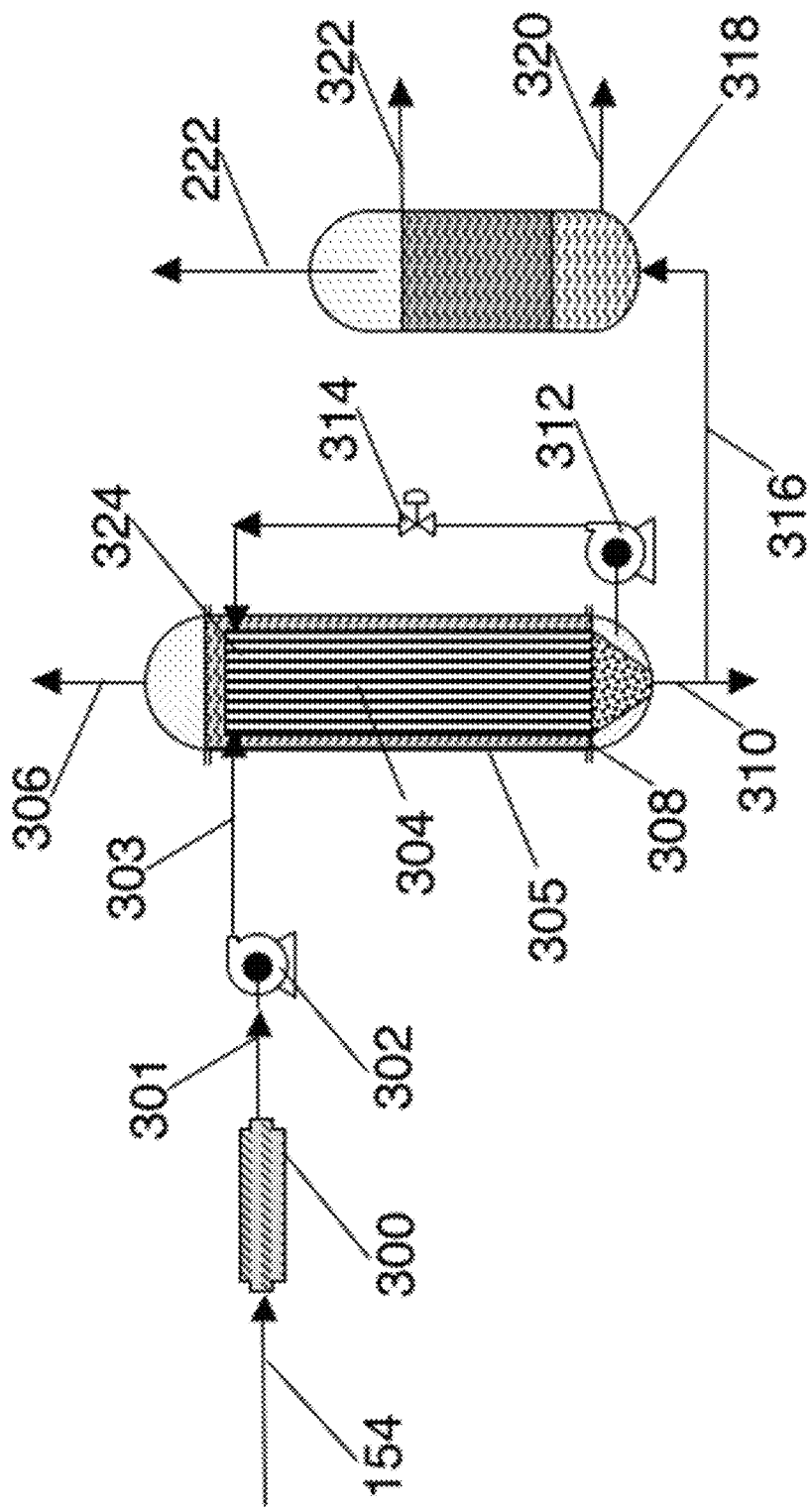
FIG. 14: Schematic representation of a portion of a process according to one embodiment of the present invention.

FIG. 14 shows in yet another embodiment how simplified the Fischer-Tropsch process can become in this new steam/$CO_2$ reforming process of waste conversion with recycle streams. Referring to FIG. 14, the cleaned and warm syngas 154 from the kiln 104 shown in FIG. 13 is passed into an air cooler 300 where it is temperature-controlled to about 180° C. (350° F.) at the exit of the air cooler 301. This stream 301 is then fed to the compressor 302 where the pressure is increased from around one atmosphere (15 psig) to 3.5 MPa (468 psig) at its outlet 303 which feeds the Fischer-Tropsch reactor 305 containing a Fischer-Tropsch catalyst 304 within its vertical tubes. This reactor carries out the synthesis reactions making a range of hydrocarbons from $CH_4$, light hydrocarbons up to heavy hydrocarbon paraffins while releasing heat.

The reaction below shows how the syngas produced in reaction [1] above can be used to make high carbon-content products such as high density, unsaturated paraffin wax as a means of sequestering carbon in a product that has significant commercial value. The other compounds formed can be recycled back into reaction [1] so that they are not released to the environment. Also there are some $CO_2$, $H_2$ and $H_2O$ that can be recycled as well from the shift converters and PSA units. Again, $C_2H_4$ is being used to represent the large range of light hydrocarbon gases for simplicity of discussion.

$$3.68CO + 2.67H_2 \rightarrow 0.055C_{20}H_{30} + 0.55C_2H_4 + 1.47CO_2 + 0.734H_2O \quad [2]$$

The temperature, pressure, $H_2/CO$ ratio of the syngas, and the residence time together control the molecular range of the Fischer-Tropsch products 316 that is then fed into the separator 318. The mixture of hydrocarbons gravimetrically separates here into three fractions: water 320, paraffins 322 and light gases overhead 222. In some embodiments there is a simple process, not requiring complex distillation, crystallization, or boiling. And it is this interfacing with the steam/$CO_2$ reforming kiln and the fuel cell that makes such a simplification possible and novel.

Figure 15:
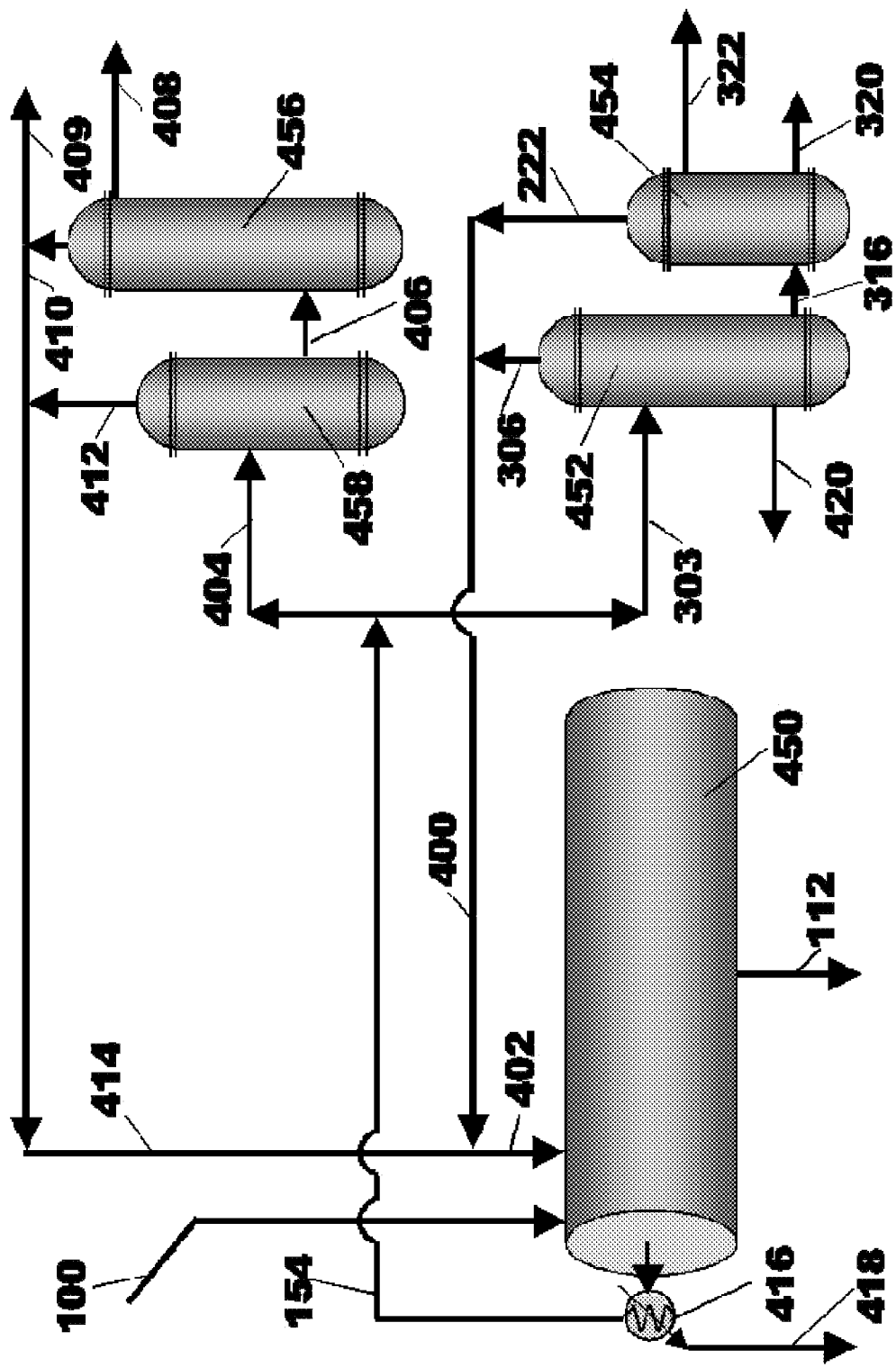
FIG. 15: Process schematic showing how a waste stream can be made to release energy without having to burn the waste or the syngas according to one embodiment of the present invention.

Yet other embodiments of the present invention include the use of other Fischer-Tropsch reactor concepts different from the conventional catalyst—packed, multi-tube (i.e. shell and tube) exothermic but isothermal reactor. Such a reactor can consist of a spiral heat exchanger where the catalyst is placed in the spiral annular regions. Such a design is shown in FIG. 15 that shows the spiral heat exchange Fischer-Tropsch Reactor wherein the syngas feed 303 (or 86 in FIG. 13 or 154 in FIG. 14) enters into the spiral annuli 512 that are packed with supported catalyst. The converted syngas consisting of the light gases together with some un-converted syngas that leaves from nozzle 222. These annuli are immersed in water between the spirals with its level controlled just above the end of the annuli. The exothermic heat boils the water to make steam that is used to feed a steam/turbo generator. The boiler feedwater enters via a nozzle. At the bottom of the reactor the liquid paraffin wax forms within and drains out the exit after it leaves the nozzle. Paraffin wax recycle from the separator 318 (shown in FIG. C), enters the outer spiral annulus through a nozzle. In one embodiment, there is a square array of fin tubes are surrounded by a square baffle so the syngas enters into a side nozzle and flows down under the bottom of the baffle and up the inside thru all the fins and exits thru nozzle at the vessel top. FT liquid forming on the catalyst surface drains down to bottom of fin tubes, drips into bottom pool, and exits thru bottom nozzle. In still further embodiments, all of the surfaces of the fins having a catalyst on the surface are contiguous. This arrangement of catalysts on the fin surfaces has provided a surprising advantage, which is the ease in lighting off the reaction process.

Finally, FIG. 15 describes how a waste stream can be made to release energy without having to burn the waste or the syngas. At the same time the waste can be converted into use carbon-containing fertilizer, hydrogen fuel, and a carbon-sequestering, high-carbon content product of important commercial value, such as unsaturated, high-density paraffin wax.

Referring to FIG. 15, the waste stream enters the process as stream 100 into rotary kiln 104 where it is steam/$CO_2$ reformed via the chemistry in reaction [1] above to form a high-hydrogen content syngas stream 154 where its high temperature heat is used in boiler 416 to produce steam 418, as well as a high carbon content product steam 112 that contains glass and metal as well as a nitrogen-free, high Potassium-Phosphorous (PK) fertilizer solid particulate of commercial value. The reaction in kiln 104 uses light gases, $CO_2$, and steam recycled as 402 from downstream process units consisting of shift converter 458, pressure-swing absorber 456, Fischer-Tropsch reactor 452 and its paraffin product separator 454. This recycle stream 402 comes from the combined streams 400 made up of 222 and 306 plus stream 414 made up of streams 410 and 412. The syngas 154 produced in kiln 104 is split into two streams 303 and 404, with 303 feeding the Fischer-Tropsch units 452 and 454 producing paraffin product 322 and stream 404 feeding the Shift 458 and PSA 456 that produce hydrogen product 408 and optional $CO_2$ at 409. In addition, the Fischer-Tropsch unit 452 is exothermic and produces steam 420 that can be used to drive a steam turbine to make electricity to run the plant and be exported for sale. Water streams 316 and 320 are used to makeup boiler feedwater. One result of this linkage and interface of the three process blocks of steam-reforming of waste to the Shift/PSA and the Fischer-Tropsch is to convert the waste to hydrogen fuel and into high-carbon PK fertilizer and carbon-sequestering paraffin with a release of heat. And this is done preferably without burning the waste and without releasing the huge amounts of greenhouse gases typical of a combustion process. Various embodiments of the present invention pertain to various apparatus and methods of destroying waste and producing steam, heat and useful products in the carbonless economy of the future.

FIG. 15 shows the use of a conventional indirectly-fired, calcining kiln 1 where the hot syngas exiting from the steam/$CO_2$ reformer, 50 can heat recycle carbon dioxide gas or air in stream 93 to supply the indirect heat to the kiln to take over from the natural gas burners commonly used. Now referring to FIG. 15, the above kiln 1 is shown interfaced to the shift/PSA unit 98 or 452 using its exhaust recycle 306 and the Fischer-Tropsch process 454 recycling the methane and light hydrocarbon gases via 222 back to the steam/$CO_2$ reforming kiln. These streams involving the waste 100, the shift/PSA unit exhaust recycle 236 and the Fischer-Tropsch overhead stream 222 are combined with the proper amount of steam 4 to carry out the steam/$CO_2$ reforming inside the kiln 104. Or this heat from heat exchanger 114, can be used to heat the recycle gas stream. These two methods of heat integration can be used in combination as well.

This reaction equilibrium favors the $H_2$ and CO at temperatures around or above 700° C. (1300° F.) so that when the syngas moves from the conventional calcining kiln 1 in FIG. 13 into the steam/$CO_2$ reformer 50, which involves temperatures around 1050° C. (1900° F.), so that this reaction is almost 100% completed. Following this reactor 50, stream 112 passes into heat exchanger 114 whereas option #1 in an inert gas, such as $CO_2$ produced elsewhere in the process, or outside air is heated by the very hot syngas in steam to be fed via stream into a series of multiple indirect burners 93 of the conventional kiln. These burners, conventionally used for natural gas, would be replaced with an injection jet that would supply the hot gas directly into the oven-furnace area of the conventional kiln. Or as option #2 this heat from heat exchanger 206, can be used to heat the recycle gas stream 236. These two methods of heat integration can be used in combination as well. The rest of the process in some embodiments is substantially the same as in FIG. 13.

Example #3: $CO_2$ Enriched Syngas

A further improvement in the reforming reaction which involves a substoichiometric amount of steam but has the light hydrocarbon Fischer-Tropsch and shift/PSA overhead represented for simplicity by $C_2H_4$, plus $CO_2$ and $H_2$, added.

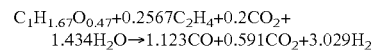

In this case, the reformation reaction is allowed to form $CO_2$ in the syngas, such that the stoichiometric ratio of $(H_2-CO_2)/(CO+CO_2)=1.42$ which is favorable for the Fischer-Tropsch reaction as follows:

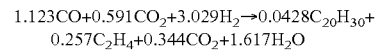

This achieves an increase in the amount of paraffin formed and greenhouse-problematic light hydrocarbons and $CO_2$ are entirely recycled back into the reformer, with a small portion of the water condensed as product water. Thus, the use of Fischer-Tropsch is further simplified. As before, the $CH_4$ is produced as the major part of the waste light gases coming off the tops of the Fischer-Tropsch gravity separator. No distillation is required. Any other light gases that are also carried along with the waste $CH_4$ can go back to the steam reformer as well. In some embodiments there are no $CO_2$ emissions since the $CO_2$ formation in the Fischer-Tropsch is recycled back into the reformer.

In FIG. 13 what has been achieved in this case is the substantial or complete elimination (i.e. stream 216 is zero) of the Shift/PSA process step at a capital savings. Likewise, in FIG. 15, stream 409 is zero. Some embodiments of the present invention accomplish near-total or total sequestration of the carbon in the waste by the formation of the high carbon content paraffin wax. Yet other embodiments contemplate other Fischer-Tropsch products that can be selected that will accomplish carbon sequestration. Commercially, there may be be an economic optimum situation where one may not want to sequester all of the carbon in the waste, but this example shows that this is theoretically possible.

Example #4: Process Flowsheet Mass Balance with Fischer-Tropsch

The process flowsheet layout based on FIG. 15, but with the process details, was completed and the mass balance done where the flow split of sending syngas to Shift/PSA system and to Fischer-Tropsch was varied. The chemistry within the steam reformer was given in reaction [1] above and in the Fischer-Tropsch unit in reaction [2] above. The results have been summarized in Table 2 below, showing how the products of the waste-to-energy plant, such as hydrogen, water carbon dioxide and paraffin was can be varied depending on the needs of the customer and the marketplace. The process choices can set the products that are made in some embodiments. The case shown is for wet waste with 15% water and a scale of 4 tonnes/day.

TABLE 2

| Shift PSA % | Fischer Tropsch % | H$_2$ Recycle | H$_2$ Kg/day | Water Kg/day | CO$_2$ Kg/day | Paraffin Kg/day | Net Electricity kWe |
|---|---|---|---|---|---|---|---|
| 62 | 38 | Low | 490 | −1547 | 6587 | 859 | 185 |
| 62 | 38 | Hi | 395 | −922 | 5823 | 1093 | 235 |
| 50 | 50 | Hi | 254 | 0 | 4096 | 1441 | 310 |
| 38 | 62 | Hi | 232 | 229 | 4416 | 1526 | 328 |
| 19 | 81 | Hi | 46 | 1475 | 2888 | 1984 | 426 |
| 0 | 100 | Low | 0 | 2264 | 1928 | 2290 | 492 |
| 0 | 100 | Hi | 0 | 3842 | 0 | 2875 | 618 |
| 0 | 100 | OptCO$_2$ | 0 | 1594 | 0 | 3851 | 861 |

As the process option is shifted more toward Fischer-Tropsch, more paraffin, water, and electricity products are made and less hydrogen fuel produced. With the various Fischer-Tropsch, no hydrogen and no carbon dioxide are produced and the amount of water, paraffins, and electricity are maximized. The electricity is a net number, after the internal electricity consumption within the plant is removed and used. The last line in Table 2 covers the case presented in Example #3, showing a great increase in Fischer-Tropsch product as well as electricity generated. Our experimental work has confirmed the mechanism discussed above from the actual measured production of FT wax, FT water and FT hydrocarbon product.

Example #5: Process Flowsheet Heat & Mass Balance for Increased Hydrogen

The process flowsheet layouts are given in FIGS. 13, and 14 showing the recycle stream going back to the rotary kiln. This example covers the case when the off-gases from the hydrogen purification and CO$_2$ extraction steps are the recycle stream going back to the kiln.

The detailed heat and mass balance for this flowsheet for maximizing hydrogen production using a cellulose feed was done by a commercial process simulator. The purpose of this optimization was to maximize the hydrogen production, minimize the need for electric grid power to operate the plant, and produce dry ice (liquid carbonic) product. The feedstock in this example is the dimer of cellulose, called cellubiose. This dimer portion of the large cellulose chain is replicated some 25,000 to 250,000 times.

The biomass enters the rotary kiln steam reformer as a solid and/or liquid phase together with the recycle gases. Within the kiln this mixture is heated, volatiles are vaporized, solids are chemically broken and decomposed, and the mixture is further heated as it moves from left to right through the kiln. At the end of the kiln, solids are removed. These solids are about 15% (by mass) of the biomass feed. With an agricultural or forest biomass feedstock, this solid product stream is a valuable freely-flowing, gravel-like, slow-release form of PK fertilizer. The gases generated inside the kiln react with the water that enters with the biomass and with any additional water that comes with the recycle stream. The steam/carbon dioxide reforming chemical reaction is endothermic (it requires supplying energy) and occurs as the key step in the process generating a syngas stream consisting of hydrogen, carbon monoxide, carbon dioxide, water and other light gases, such as methane, ethane, ethylene, etc.

The hot syngas leaving the rotary kiln is heated, mixed with hot superheated steam, and enters the vertical steam reformer where it is further heated to complete the steam/carbon dioxide reforming reaction producing the highest concentration of hydrogen with the least amount of other organic contaminants, such as higher hydrocarbons and aromatics.

Various embodiments expressed herein address biomass phase-change as a solid-to-vapor chemical decomposition. The biomass is decomposed into a vapor by breaking the chemical bonds. This process is not the classical solid-to-liquid transition (heat of melting), or the liquid-to-vapor transition (heat of vaporization). As these molecular fragments move through the kiln, the temperature increases, causing further decomposition by the hydroxyl radical attacking and breaking the next stronger bond, such as carbon-carbon bonds. The last and toughest bonds to be attacked are the aromatic carbon-carbon bonds. This decomposition results in the aromatic ring coming apart which creates other organic gases such as ethane, ethylene and butyne. Small amounts of these gases can recombine to form other very stable aromatic compounds.

This very hot syngas leaving the steam reformer passes through heat exchangers to recover energy to supply heat to processing equipment or to generate steam for process use and/or power generation. The cool hydrogen-rich syngas is passed to the hydrogen purification section, shown in the on the right-hand portion of the graphic in FIG. 13, where the carbon monoxide is reacted with more superheated steam to form carbon dioxide and additional hydrogen as well as release of heat. This rich hydrogen gas mixture is purified in a commercial pressure swing adsorption unit yielding a hydrogen stream ranging from 99.9% to 99.99% purity. The remaining carbon dioxide and other light gases pass overhead into the carbon dioxide recovery system. Here a clean carbon dioxide stream is produced that feeds a commercial carbon dioxide liquefaction plant where either liquid carbon dioxide (liquid carbonic) or dry ice is produced. The remaining light gases are recycled to the kiln.

Surprisingly, it was found possible to recover enough heat from the exothermic shift converter to preheat the recycle gas and add enough heat to the material feeding the kiln to change its phase to a vapor and heat it to 400 to 500° C. Leaving the exit of the kiln is the freely-flowing granular residue, 15% of the biomass on a dry basis, which is formed in the rotary kiln. This residue is high in carbon content. In this way, the heat added to the commercial kiln is supplied by recovered process heat and trimmed with electric heat to control the reaction temperature at 400° to 500° C.

The simulation modeled the commercial steam reformer. It mixed the product from the rotary kiln at 1 atmosphere with superheated steam added at 300 PSIA and 267° C. Waste heat from the syngas heats the steam reformer feed to around 875° C. The steam reformer was modeled as an isothermal reactor. The heat added to the commercial steam reformer is supplied by recovered process heat and trimmed with electric heat to control the reaction temperature at around 875° C.

The simulation modeled a commercial heat exchanger cooling the steam reformer hot syngas effluent while recovering energy to be returned to the process. Next, water is condensed out of the syngas and removed in a commercial vapor liquid separator. The vapor leaving this separator flows to a commercial carbon bed adsorber, where small amounts of aromatic organic compounds are removed. The vapor leaving this bed flows to a 3-stage compressor that increases the process pressure to 300 PSIA for the downstream shift converter and pressure swing adsorption (PSA) H$_2$ recovery. A heat exchanger module removes the heat of compression cooling the vapor to 260° C. In practice, the compressor uses first and second stage intercoolers and the 3-stage after-cooler.

The syngas from the compressor is mixed with superheated steam and the combined flow enters the carbon monoxide shift converter. The shift converter is modeled as an adiabatic reactor. This reactor converts water and carbon monoxide to desired carbon dioxide and hydrogen products. Energy is recovered in a heat exchanger. This energy is returned back to the process. The water that condenses is removed in a vapor-liquid separator. The vapor from this separator flows to a pressure swing adsorption unit where 80% of the hydrogen leaving the PSA is recovered as product with 99.9% purity. The remaining vapor leaving the PSA unit flows to the carbon dioxide recovery system, modeled as a simple separation device. In practice this equipment could be a membrane system or an amine system with a liquid carbonic and/or dry ice production unit. The vapor leaving $CO_2$ separator flows to the heat exchanger, preheating the vapor prior to feeding the rotary kiln.

One aspect of this process configuration with the major recycle loop carrying the unconverted hydrogen and other light gases from the PSA unit, is that these gases are further converted in the steam/$CO_2$ reforming units to make more hydrogen product, as used in the mass balance preferring that the hydrogen coming in with the feedstock must leave the process as the hydrogen product. Additional or higher conversion stages in the PSA unit are not needed when this recycle loop is used.

To validate the process simulation predictions, a biomass sample of grape pomace, available in huge quantity from the wine industry, was test-run in a pilot unit as illustrated in FIG. 13, less the hydrogen purification and liquid carbonic steps, to produce the syngas stream. This measured syngas stream was compared with the Design-2 process simulation prediction below in Table 4.

TABLE 4

Comparison of Pomace Produced Syngas With Simulation Results

| Component | Test Results | Simulation Prediction |
|---|---|---|
| Hydrogen | 59.4% | 61.4% |
| Oxygen + Argon* | 0% | |
| Nitrogen* | 0% | |
| Carbon Monoxide | 32.4% | 31.3% |
| Carbon Dioxide | 2.96% | 6.2% |
| Methane | 5.1% | |
| Ethane, acetylene, ethylene | 570 ppm | <940 ppm |
| Propane** | 98 ppm | |
| Butanes** | 60 ppm | |
| Benzene** | 198.4 ppm | 1 ppb |
| C7 and above** | 380 ppm | |
| Hydrogen Sulfide** | 59.8 ppm | |
| Carbonyl Sulfide** | 1.74 ppm | |
| Methyl Mercaptan** | 16.6 ppm | |
| Carbon Disulfide** | 35.3 ppm | |

*Air leakage accounted for.
**In practice, these components will be removed by a zinc bed, carbon bed or are recycled to the kiln The comparison of the test results and the simulation prediction of syngas is excellent. The kiln and steam/$CO_2$ reformer chemical reactors' process temperatures and steam content, in the simulation, match those of the pilot demonstration.

Example #6: Digestate and Biogas

Figure 9:
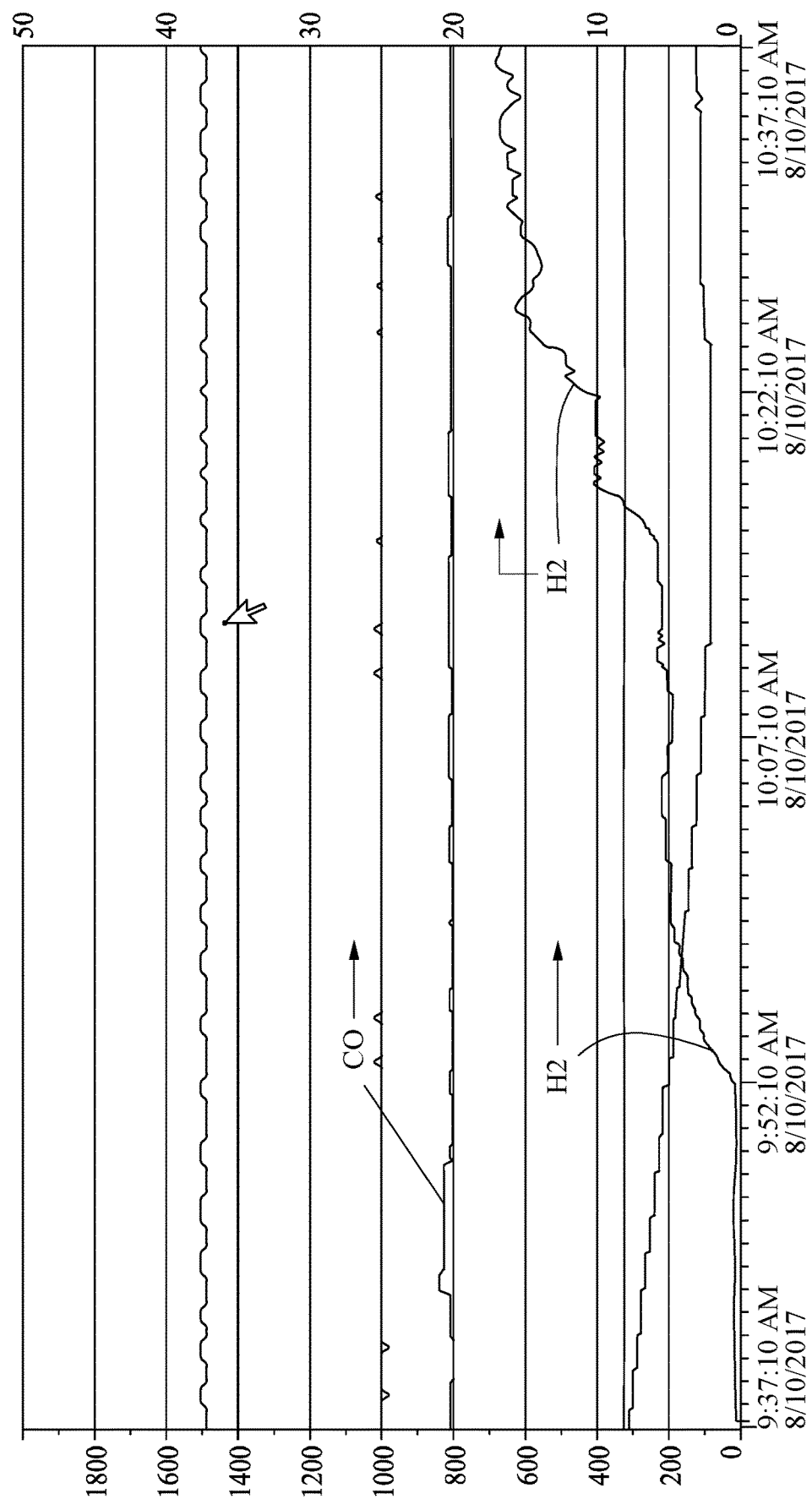
FIG. 9: H2 production from biogas and then from biogas & digestate as produced in a method according to one embodiment of the present invention.

A combined dairy digestate solids and digester biogas run according to another embodiment of the present invention was performed. First, the run was started with Biogas only (10 cc/min $CH_4$ and 20 cc/min $CO_2$—so 66% $CO_2$ as the Biogas leaving the commercial digesters. As can be seen by the increasing the blue curve in FIG. 9, the $H_2$ increased from zero and to 5% in 6 minutes with the steady state plateau in 15 minutes, at which point the digestate was fed slowly at first, reaching a plateau of 17% at the right side of FIG. 9.

Then, as can be seen in FIG. 10, as the digestate feedrate was increased to capacity, the $H_2$ rose from 17% in the center of the figure to 30% at the right of the figure. The sharp dip was the period for sampling this syngas for the GC analysis to capture the first of the high plateau. The GC showed a 27% $H_2$ level, in close agreement with the $H_2$ sensor. The $H_2$ level went on to reach 30% thereafter. And oxygen level (the orange line) remained low and near zero throughout. The $H_2$/CO ratio from this run was 2.11±0.5.

Figure 11:
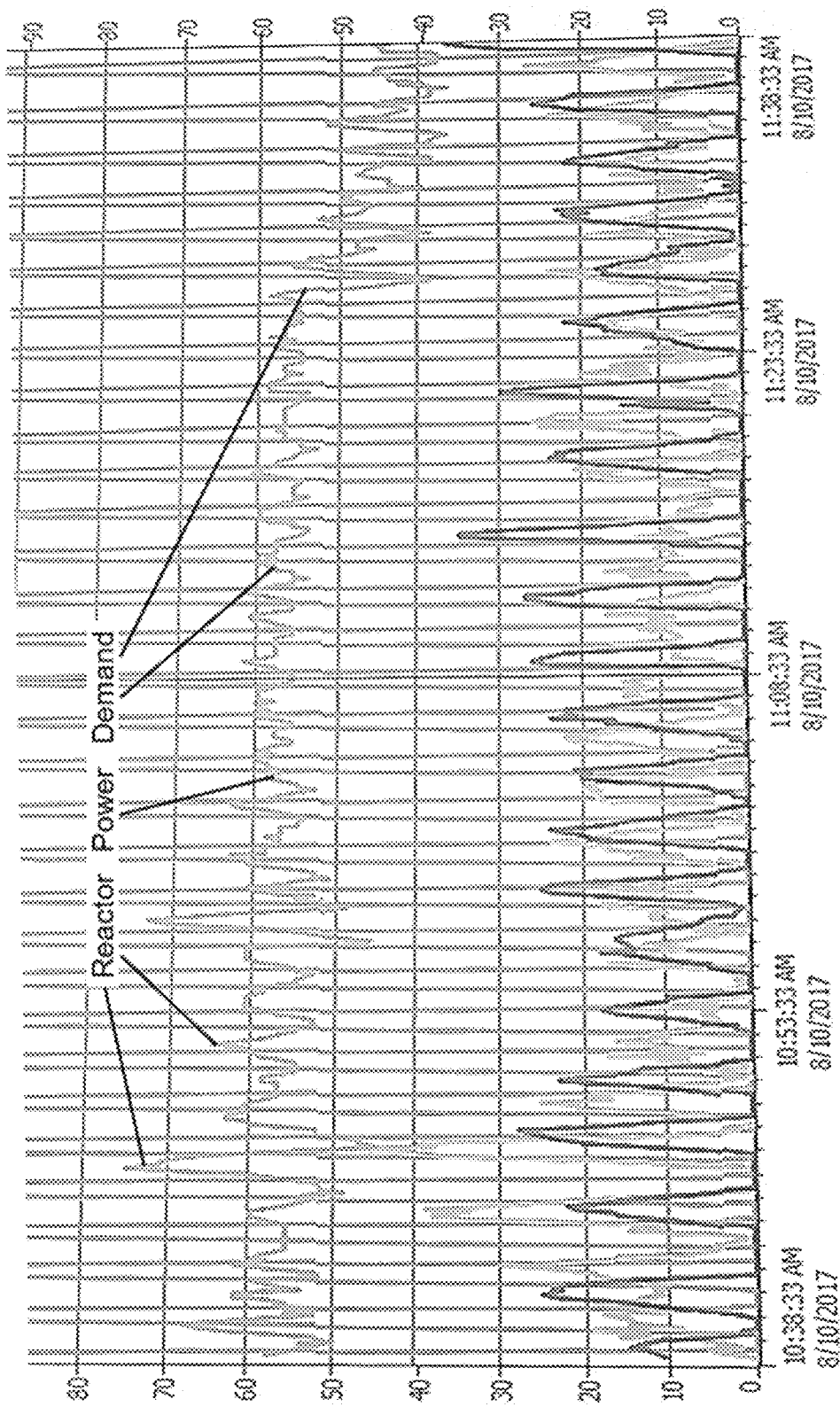
FIG. 11: Main SR reactor power demands as produced in a method according to one embodiment of the present invention.

The main SR reactor power demand at this $H_2$ plateau was 58% or 4.76 kWe, as shown in FIG. 11 as the red curve. The evenly-spaced 2 minute pulses in power are a result of the PID control system feeding power to the various heaters. These will eventually be smoothed out as each of their PID loops are tuned for more even control. With 8/10 run completion, the feed was stopped and, as can be seen in FIG. 11, the main SR reactor power demand dropped over 15 min. to 42% that is the normal idle power demand with no chemistry going on.

Also of interest in FIG. 11 is the orange curve at the left shown an increasing set of power pulses reaching 50% in the rotary reformer final section running at 1000° F. This shows that a rich clump of digestate reached the final rotary reformer section demanding increased heat for processing before going on the main SR reactor. As the feed became more uniform the orange curve was steady.

Various aspects of different embodiments of the present invention are expressed in paragraphs X1, X2, and X3 as follows:

X1. One aspect of the present invention pertains to a process that provides the interface between a steam/$CO_2$ reforming waste conversion system using organics generating syngas without a catalyst and a exothermic organic hydrocarbon synthesis reactor operating at 125 psig that recycles the light tail gases hydrocarbons off of this synthesis reactor.

X2. Another aspect of the present invention pertains to a process that provides the interface between a steam/$CO_2$ reforming waste conversion system using liquid, gas, and solid organics generating syngas and an exothermic organic hydrocarbon synthesis reactor that recycles hydrocarbons off of this synthesis reactor, and reacts them in the steam/$CO_2$ reformer operated below 1800° F., also recycling the hydrocarbons to control and help maintain a $H_2$/CO ratio from 1.5 to 3.2 of the syngas as might be desired for the synthesis reactor.

X3. Yet another aspect of the present invention pertains to a method of reforming of organic waste material. The method preferably includes producing a first stream of synthesized hydrocarbon gas including hydrogen and carbon monoxide. The method preferably includes mixing organic waste with a first portion of the hydrogen and carbon monoxide from the first stream. The method preferably includes reforming the mixture of the first stream and the waste with steam and carbon dioxide and producing a second stream of synthesized hydrocarbon gas and heat. The method preferably includes using a second portion from the second stream for said producing a first stream.

Yet other embodiments pertain to any of the previous statements X1, X2, or X3, which are combined with one or more of the following other aspects. It is also understood that any of the aforementioned X paragraphs include listings of individual features that can be combined with individual features of other X paragraphs.

Where a exothermic organic hydrocarbon synthesis reactor combined with a parallel shift converter/pressure-swing absorption unit to accomplish the conversion of the syngas to commercially-marketable hydrogen fuel, ample steam to generate electrical power for the plant and for export, and a high-carbon content liquid organic product that sequesters substantially the carbon in the waste stream—all without any burning of the waste or the syngas.

Where the light gases from the exothermic organic hydrocarbon synthesis reactor that is a Fischer-Tropsch unit are recycled back to the steam reformer for destruction and avoiding release to the environment.

Where carbon dioxide and a portion of the hydrogen from the Shift and Pressure Swing Absorber units are recycled back to the steam reformer to adjust the $H_2/CO$ ratio for optimum utilization in the Fischer-Tropsch unit.

Where small impurities in the syngas that could damage the sensitive catalysts in a high temperature fuel cell do not damage the more robust catalysts (i.e. iron or cobalt-based) in a Fischer-Tropsch unit.

Where the best clean-up of syngas impurities involves a process where there are both a high temperature filtration step and a sulfur-, chlorine-, and nitrogen-containing compound removal step as well as a chilling and condensation step downstream which includes a HEPA filter and a guard bed to protect high temperature fuel cell electrochemical catalysts.

Where the best clean-up of syngas impurities involves a process where there are both a high temperature filtration step and a sulfur-, chlorine-, and nitrogen-containing compound removal step as well as a chilling and condensation step downstream which includes a HEPA filter and a guard bed to protect Fischer-Tropsch catalysts.

Where a exothermic organic hydrocarbon synthesis reactor that is greatly simplified because its many tail or overhead streams can be used as recycle to the steam/$CO_2$ reforming process.

Where a power recovery system that involve the combined use of a shift and PSA unit as well as the Fischer-Tropsch unit to make best use of recycle streams and waste heat.

Where an exothermic reactor consists of a Fischer-Tropsch reactor.

Where an exothermic reactor consists of a methanol synthesis reactor.

Where an exothermic reactor consists of a methanation reactor.

Where heat to the kiln sections doing endothermic steam/$CO_2$ reforming is supplied by recycling the syngas through the holoflite screw to heat the waste and do reforming.

Where a recycle loop carrying the unconverted hydrogen and other light gases from the PSA unit back to the feed-end kiln, wherein these gases are further converted in the steam/$CO_2$ reforming units to make more hydrogen product, as required in the mass balance dictating that the hydrogen coming in with the feedstock must leave the process as the hydrogen product; so that in this way, additional or higher conversion stages in the PSA unit are not needed when this recycle loop is used.

Which further comprises controlling said producing a first stream to maintain a ratio of hydrogen to carbon monoxide from about one and one half to about three and two tenths.

Wherein said reforming does not include burning the waste or the portion of the first stream.

Wherein said reforming is without the use of a catalyst.

Which further comprises using the heat from said reforming to drive a heat engine and generator to produce electricity.

Wherein said producing a first stream is with a Fischer-Tropsch reaction.

Wherein said reforming is at a temperature from about one thousand five hundred degrees F. to about one thousand eight hundred degrees F.

Wherein said using a second portion includes cooling the second portion prior to said producing a first stream.

Wherein said using a second portion includes pressurizing the second portion prior to said producing a first stream.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

The invention claimed is:

1. A waste reformation system comprising:
   a hydrocarbon synthesis reactor for producing a first stream of synthesized hydrocarbon gas;
   a waste reforming conversion system for receiving organic waste, steam, and carbon dioxide and for producing a second stream of synthesized hydrocarbon gas;
   wherein the hydrocarbon synthesis reactor is in fluid communication with the waste reforming conversion system such that a first portion of the first stream is mixed with the organic waste prior to the organic waste being received by the waste reforming conversion system; and
   wherein the waste reforming conversion system is in fluid communication with the hydrocarbon synthesis reactor such that a second portion of the second stream is used for producing the first stream.

2. The waste reformation system of claim 1, further comprising means for cooling the second portion prior to said producing the first stream.

3. The waste reformation system of claim 2, wherein the means for cooling is a Brayton cycle turbine.

4. The waste reformation system of claim 1, further comprising means for pressurizing the second portion prior to said producing the first stream.

5. The waste reformation system of claim 1, wherein the hydrocarbon synthesis reactor is at least one of a Fischer-Tropsch unit and a shift converter.

6. The waste reformation system of claim 1, wherein the hydrocarbon synthesis reactor is a Fischer-Tropsch unit and a shift converter.

7. The waste reformation system of claim 1, wherein the waste reforming conversion system is a steam/$CO_2$ reformer.

8. The waste reformation system of claim 7, wherein the steam/$CO_2$ reformer is a rotary steam/$CO_2$ reformer.

9. The waste reformation system of claim 1, wherein operation of the waste reforming conversion system does not include burning the waste or the portion of the first stream.

10. The waste reformation system of claim 1, wherein operation of the waste reforming conversion system does not include use of a catalyst.

11. The waste reformation system of claim 1, wherein the hydrocarbon synthesis reactor additionally produces a carbon-containing liquid or solid product.

12. The waste reformation system of claim 11, wherein the organic waste includes carbon and wherein substantially all of the carbon in the organic waste is sequestered in the carbon-containing liquid or solid product.

13. The waste reformation system of claim 1, further comprising a heat engine in fluid communication with the waste reforming conversion system.

14. The waste reformation system of claim 1, wherein the first stream of synthesized hydrocarbon gas includes hydrogen and carbon monoxide.

15. The waste reformation system of claim 1, wherein the waste reforming conversion system is configured to operate at a temperature from about on thousand five hundred degrees Fahrenheit to about one thousand eight hundred degrees Fahrenheit.

* * * * *